US009326664B2

(12) United States Patent
Takei et al.

(10) Patent No.: US 9,326,664 B2
(45) Date of Patent: May 3, 2016

(54) ENDOSCOPE APPARATUS

(71) Applicant: OLYMPUS MEDICAL SYSTEMS CORP., Tokyo (JP)

(72) Inventors: Shunji Takei, Hachjioji (JP); Makoto Igarashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 98 days.

(21) Appl. No.: 14/452,866

(22) Filed: Aug. 6, 2014

(65) Prior Publication Data

US 2015/0022647 A1    Jan. 22, 2015

Related U.S. Application Data

(63) Continuation of application No. PCT/JP2013/083613, filed on Dec. 16, 2013.

(30) Foreign Application Priority Data

Feb. 12, 2013  (JP) .................................. 2013-024727

(51) Int. Cl.
  *H04N 9/64* (2006.01)
  *A61B 1/00* (2006.01)
  *A61B 1/05* (2006.01)
  *A61B 1/06* (2006.01)
  *G02B 23/24* (2006.01)

(52) U.S. Cl.
  CPC .............. *A61B 1/00186* (2013.01); *A61B 1/05* (2013.01); *A61B 1/0638* (2013.01); *A61B 1/0684* (2013.01); *G02B 23/2461* (2013.01); *H04N 9/64* (2013.01); *A61B 1/00009* (2013.01)

(58) Field of Classification Search
  CPC ...................................................... H04N 9/64
  USPC ........................................................... 348/70
  See application file for complete search history.

(56) References Cited

U.S. PATENT DOCUMENTS 4,621,284 A  *  11/1986  Nishioka .............. A61B 5/1076
                                                    348/135
2011/0017923 A1 *  1/2011  Kubo ................. A61B 1/00009
                                                    250/458.1

FOREIGN PATENT DOCUMENTS

JP        60-262001 A    12/1985
JP      2009-291347 A    12/2009

(Continued)

*Primary Examiner* — Christopher S Kelley
*Assistant Examiner* — Jonathan Messmore
(74) *Attorney, Agent, or Firm* — Scully, Scott, Murphy & Presser, PC

(57) ABSTRACT

An endoscope apparatus includes an illuminating section capable of irradiating a subject with a light in a first wavelength band and light in a second wavelength band, an image processing section including a color filter configured by a plurality of filters, the image processing section generating, from two image pickup signals respectively generated in a first pixel and a second pixel that respectively receive light in a predetermined wavelength band and light in a wavelength band different from the predetermined wavelength band among return lights from the subject, first and second image signals, a control section that determines whether the two image pickup signals can be separated into the first and second image signals, and an illumination control section that performs irradiation in a time division manner or simultaneous irradiation according to a determination result whether the separation is possible or not.

7 Claims, 17 Drawing Sheets

(56) References Cited

FOREIGN PATENT DOCUMENTS

| | | | |
|---|---|---|---|
| JP | 2010-184047 A | 8/2010 | |
| JP | 2011-194028 A | 10/2011 | |
| WO | 20081105370 A1 | 9/2008 | |

* cited by examiner

FIG. 2
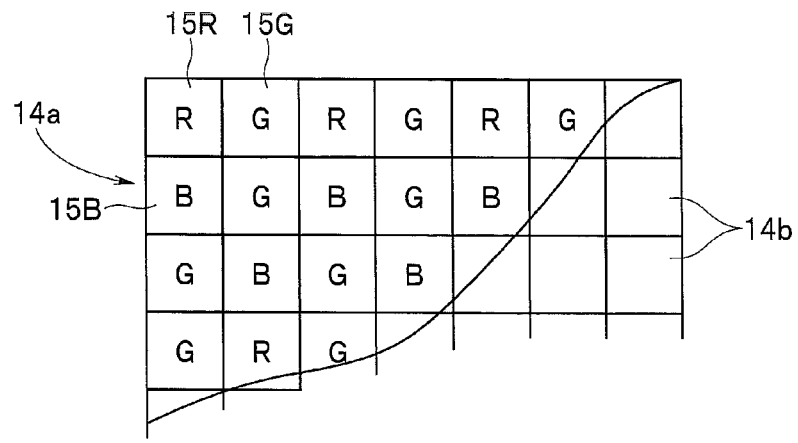
FIG. 3
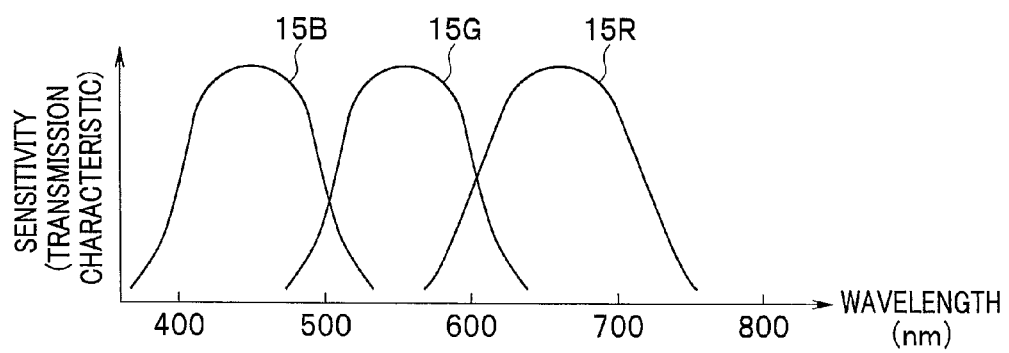
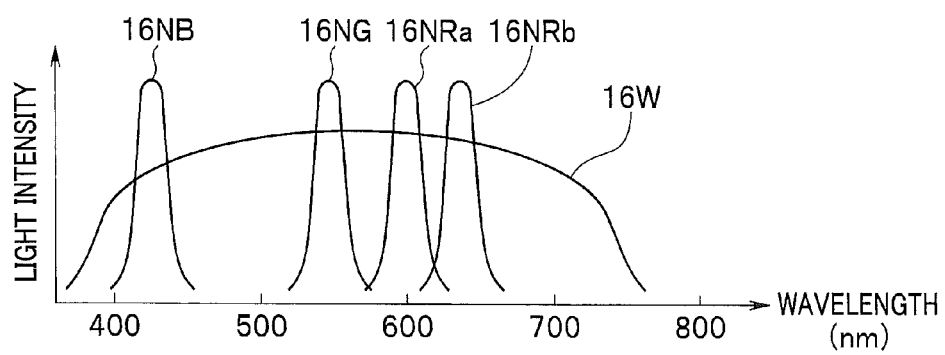

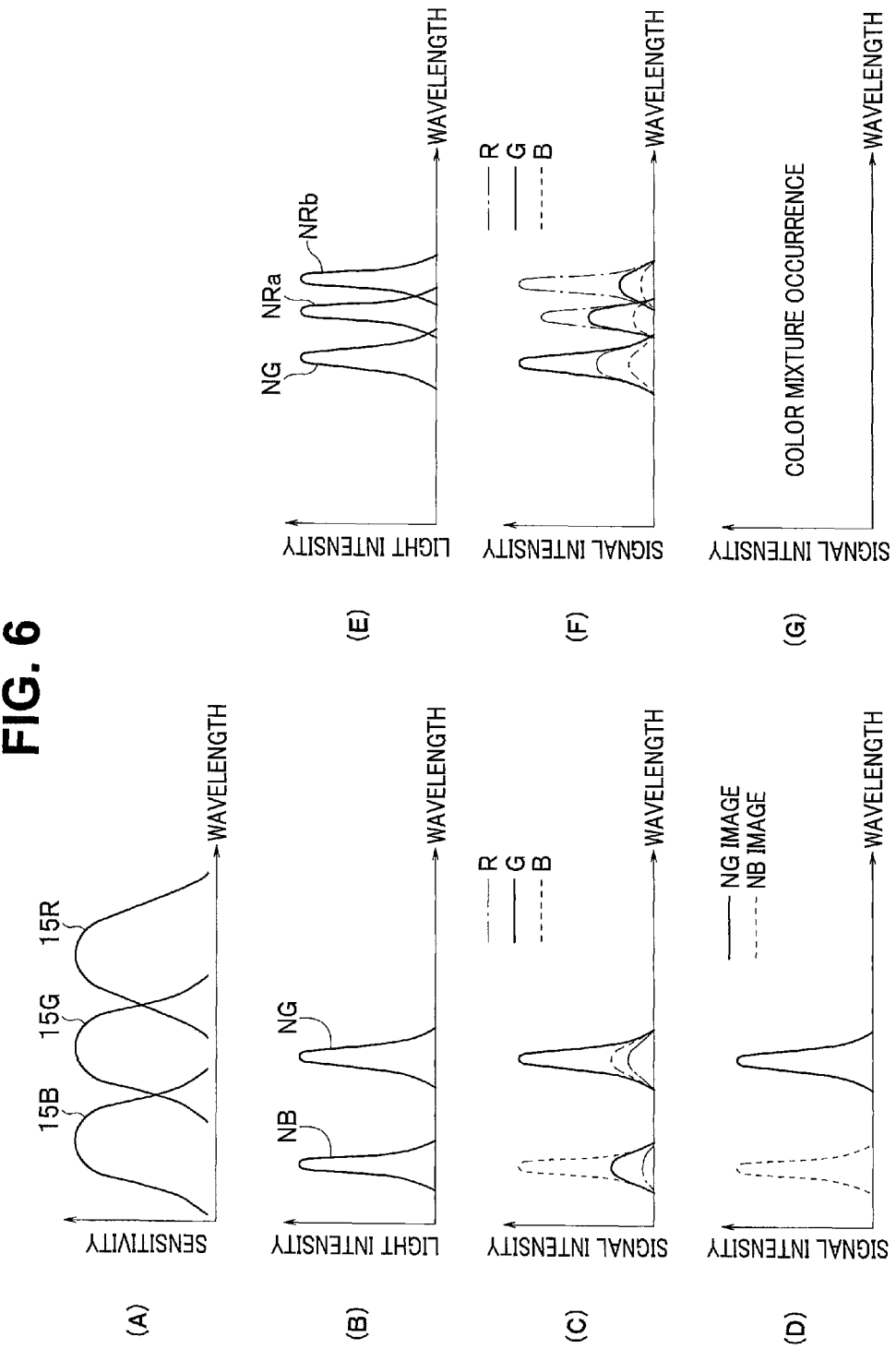

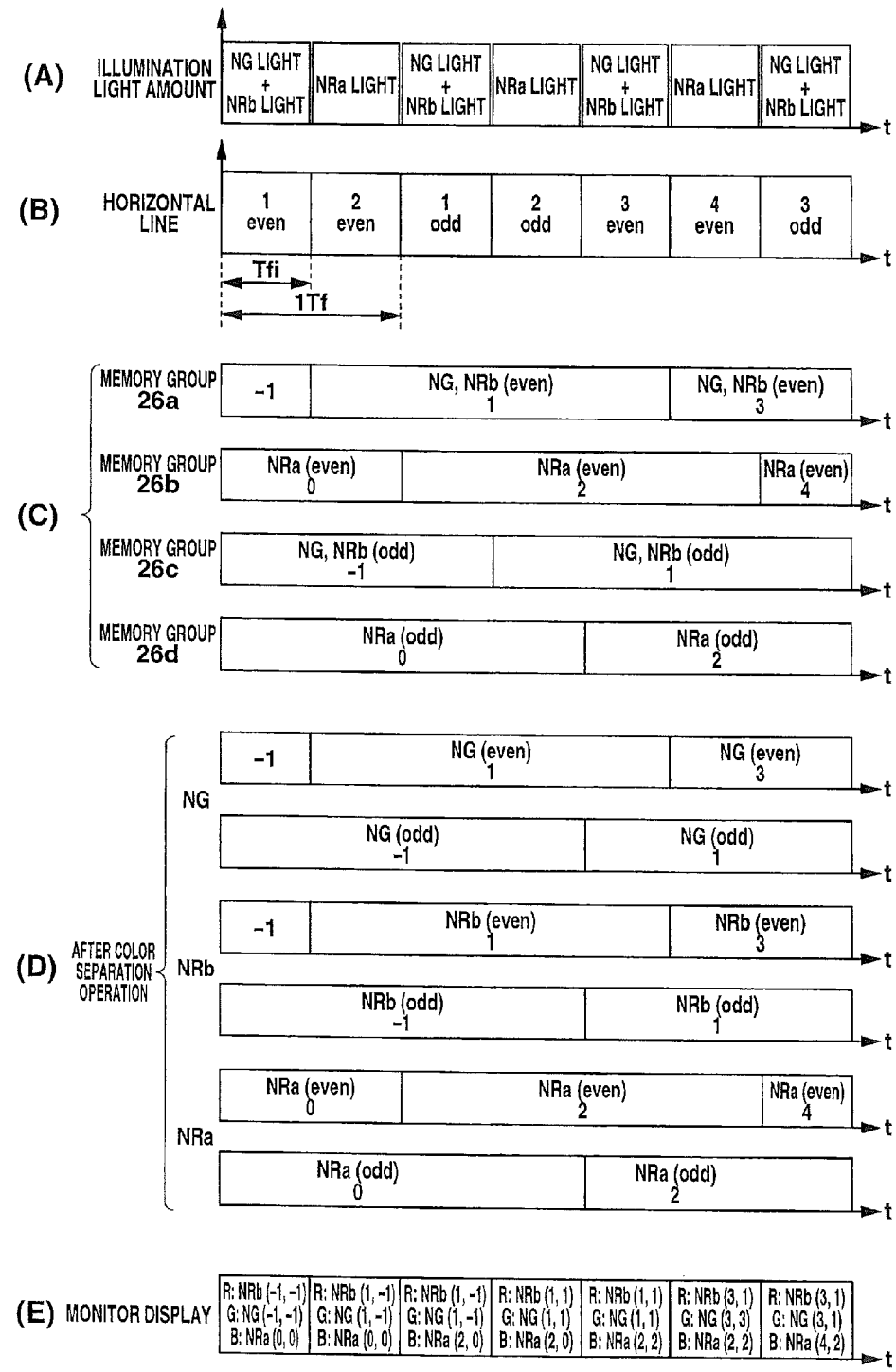

ENDOSCOPE APPARATUS

CROSS REFERENCE TO RELATED APPLICATION

This application is a continuation application of PCT/JP2013/083613 filed on Dec. 16, 2013 and claims benefit of Japanese Application No. 2013-024727 filed in Japan on Feb. 12, 2013, the entire contents of which are incorporated herein by this reference.

BACKGROUND OF THE INVENTION

1. Field of the Invention

The present invention relates to an endoscope apparatus that performs image pickup using an image pickup device including a color mosaic filter.

2. Description of the Related Art

An endoscope including an image pickup device at a distal end portion of an insertion portion is widely used in a medical field and an industrial field.

In recent years, according to an increase in the number of pixels of an image pickup device, an image pickup device for color provided with a color filter in an image pickup device has a merit that color image pickup can be performed under white illumination and problems of color drift and a decrease in a frame rate can be further avoided than an image pickup device for monochrome in which a color filter requiring frame sequential illumination is not provided.

On the other hand, besides being used in an application for performing a normal endoscopy under illumination of white light, there is also a need for performing an endoscopy under special illumination light.

For example, a conventional example of Japanese Patent Application Laid-Open Publication No. 2010-184047 discloses an endoscope apparatus that performs a normal observation by normal illumination light and a special light observation by special light illumination using a charge coupled device (abbreviated as CCD) including color filters of R, G, and B.

When a simultaneous photographing mode is selected, a light source for normal illumination light and a light source for special illumination light alternately or simultaneously irradiate the normal illumination light and the special illumination light in accumulation period units of the CCD. The CCD in an inter-line transfer type immediately starts, in a 2n-th image pickup operation, charge accumulation in a light-receiving element after reading out and transferring a signal charge to a vertical CCD from the light-receiving element in a 2n−1-th image pickup operation. After the charge accumulation, the CCD performs readout and transfer according to a readout pulse. After the readout and transfer, the CCD retains the signal charge in the vertical CCD until horizontal transfer of the signal charge by the 2n−1-th image pickup operation ends.

SUMMARY OF THE INVENTION

An endoscope apparatus according to an aspect of the present invention includes: an illuminating section capable of irradiating, as illumination light for illuminating a subject, a light in a first wavelength band and light in a second wavelength band having a wavelength band different from the light in the first wavelength band; an image processing section for generating, from an image pickup signal generated in a first pixel that receives light in a predetermined wavelength band among lights from the subject on which the illumination light is irradiated and an image pickup signal generated in a second pixel that receives light in a wavelength band different from the light in the predetermined wavelength band among the lights from the subject, a first image signal and a second image signal respectively allocated to different color channels of a display section for displaying an observation image of the subject; a control section that determines whether an image pickup signal of the subject corresponding to the light in the first wavelength band and an image pickup signal of the subject corresponding to the light in the second wavelength band can be separated into the first image signal and the second image signal; and an illumination control section that simultaneously irradiates, when the control section determines that the image pickup signal of the subject corresponding to the light in the first wavelength band and the image pickup signal of the subject corresponding to the light in the second wavelength band can be separated into the first image signal and the second image signal, the light in the first wavelength band and the light in the second wavelength band and irradiates, in a time division manner, when the control section determines that the image pickup signals cannot be separated into the first image signal and the second image signal, the light in the first wavelength band and the light in the second wavelength band.

BRIEF DESCRIPTION OF THE DRAWINGS

FIG. 2 is a diagram showing a configuration example of a color filter provided in an image pickup device;

FIG. 3 is a diagram showing a transmission characteristic of the color filter and light emission characteristics of a white LED and an LED in a narrowband that configure a light source unit;

FIG. 6 is an explanatory diagram of illumination and image pickup operation in the first embodiment;

FIG. 17 is a timing chart for operation explanation in a modification of the third embodiment.

DETAILED DESCRIPTION OF THE PREFERRED EMBODIMENTS

Embodiments of the present invention are explained below with reference to the drawings.

First Embodiment

Figure 1:
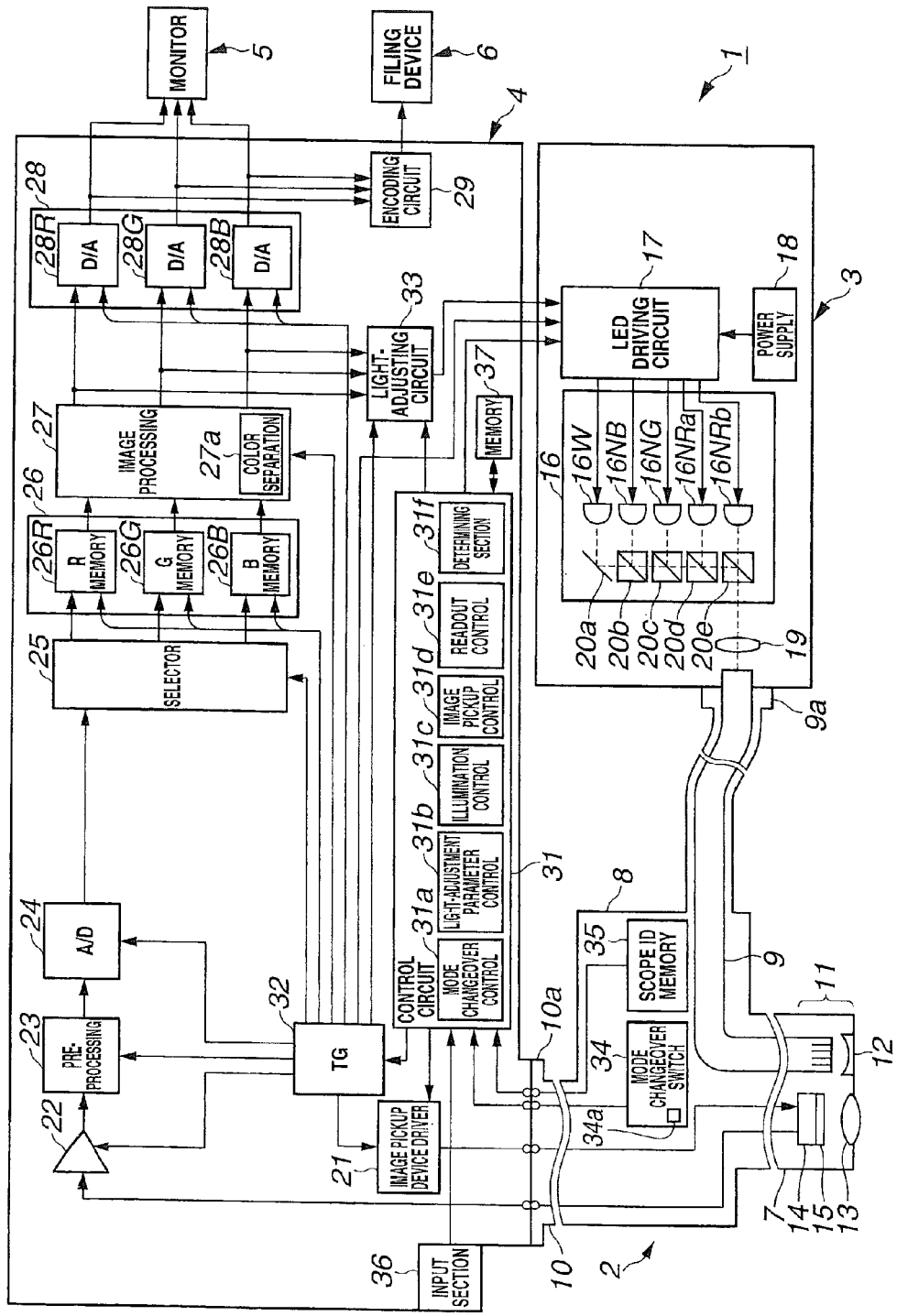
FIG. 1 is a diagram showing an overall configuration of an endoscope apparatus in a first embodiment of the present invention.

As shown in FIG. 1, an endoscope apparatus 1 in a first embodiment of the present invention includes an endoscope 2 inserted into a subject, a light source device 3 that supplies illumination light to the endoscope 2 detachably connected thereto, a video processor 4 functioning as a signal processing device that performs signal processing for an image pickup signal picked up by image pickup means of the endoscope 2, a monitor 5 that displays an image signal outputted from the video processor 4, and a filing device 6 that records the image signal.

The endoscope 2 includes an insertion portion 7 inserted into the subject and an operation portion 8 provided at a rear end (a proximal end) of the insertion portion 7. A light guide connector 9a at a distal end of a light guide 9 extended from the operation portion 8 is detachably connected to the light source device 3. Illumination light emitted from the light source device 3 is made incident on an incident end face of the light guide 9 of the light guide connector 9a.

The incident illumination light is emitted from a distal end face of the light guide 9 arranged at a distal end portion 11 of the insertion portion 7 through insides of the operation portion 8 and the insertion portion 7 to an outside by the light guide 9 through an illumination lens 12 attached to an illumination window and irradiated on an object such as an affected part (a region in the subject) to illuminate the object.

An observation window is provided in the distal end portion 11 to be adjacent to the illumination window. An objective lens 13 that refracts return light (reflected light) from the object and forms an optical image of the return light is attached to the observation window. An image pickup surface of an image pickup device 14 functioning as image pickup means is arranged in a position of the image formation. A color filter 15 that optically performs color separation is provided on the image pickup surface of the image pickup device 14.

FIG. 2 shows a configuration of the color filter 15. Pixels 14b configuring a light-receiving element, which performs photoelectric conversion, are two-dimensionally arranged on an image pickup surface 14a of the image pickup device 14. In front of the respective pixels 14b, R, G, and B filters 15R, 15G, and 15B, which respectively transmits lights in wavelength bands of red (R), green (G), and blue (B), are regularly arranged in pixel units and the color filter 15 of an improved Bayer system is formed. Note that, in a case of FIG. 2, pixels are arrayed as units of the color filter 15 in which eight pixels are color-separated from colors for four pixels in a longitudinal direction and colors for two pixels in a lateral direction. The video processor 4 generates R, G, and B signals for each arrayed pixels serving as units.

FIG. 3(A) shows a transmission characteristic of the R, G, and B filters 15R, 15G, and 15B configuring the color filter 15 with respect to a wavelength. FIG. 3(A) also shows a characteristic of sensitivity in the image pickup device 14 including the color filter 15 with respect to the wavelength. As explained below, according to application of an image pickup device driving signal from an image pickup device driver 21, the image pickup device 14 performs color separation in the R, G, and B filters 15R, 15G, and 15G and outputs a photoelectrically converted signal as a return light signal.

As shown in FIG. 1, the light source device 3 includes a plurality of light-emitting diode units (abbreviated as LED units) 16, an LED driving circuit 17 that drives the LED units 16, a power supply circuit 18 that supplies electric power for driving to the LED driving circuit 17, and a condenser lens 19 that condenses illumination lights of the LED units 16 and makes the lights incident on the light guide 9.

The LED units 16 include a white LED 16W that generates white light for performing a normal light observation (abbreviated as WBI observation) in a normal light observation mode (abbreviated as WBI observation mode) and four LEDs 16NB, 16NG, 16NRa, and 16NRb functioning as a plurality of narrowband LEDs that generate a plurality of different narrowband lights for performing a narrowband light observation (abbreviated as NBI observation) in a narrowband light observation mode (abbreviated as NBI observation mode).

The LED units 16 include, as (light source means or) illuminating means for the NBI observation mode, the LED 16NB and the LED 16NG that emit lights in a narrowband in respective wavelength bands of B and G and an LED 16NR1 and an LED 16NR2 that respectively emit lights in a narrowband in a wavelength band of R.

The LED units 16 include a mirror 20a and half mirrors 20b to 20e arranged in front of optical paths of the white LED 16W, the LED 16NB, the LED 16NG, the LED 16NR1, and the LED 16NR2.

After being reflected by the mirror 20a, white light of the white LED 16W is transmitted through the half mirrors 20b to 20d and, after being reflected by the half mirror 20e, condensed by the condenser lens 19 and made incident on the light guide 9. After being reflected by the half mirror 20b, light in the narrowband of the LED 16NB is transmitted through the half mirrors 20c and 20d and, after being reflected by the half mirror 20e, made incident on the light guide 9 through the condenser lens 19.

After being reflected by the half mirror 20c, light in the narrowband of the LED 16NG is transmitted through the half mirror 20d and, after being reflected by the half mirror 20e, made incident on the light guide 9 through the condenser lens 19. After being reflected by the half mirror 20d, light in the narrowband of the LED 16NR1 is reflected by the half mirror 20e and made incident on the light guide 9 through the condenser lens 19. Light in the narrowband of the LED 16NR2 is transmitted through the half mirror 20e and made incident on the light guide 9 through the condenser lens 19.

FIG. 3(B) shows light emission characteristics of the white LED 16W, the LED 16NB, the LED 16NG, the LED 16NRa, and the LED 16NRb. The white LED 16W has a light emission characteristic for covering a visible wavelength band (approximately 380 nm to 750 nm). On the other hand, the LED 16NB, the LED 16NG, the LED 16NRa, the LED 16NRb respectively have light emission characteristics for emitting lights in the narrowbands of the wavelength bands of B and G and the wavelength band of R.

In this case, one light in the narrow band of the LED 16NB and one light in the narrow band of the LED 16NG are respectively included in the respective wavelength bands of the B filter 15B and the G filter 15G. On the other hand, two lights in the narrowbands of the two LEDs 16NRa and 16NRb are included in the wavelength band of the R filter 15R. A rather large ratio of components of light by the LED 16NRa on a short wavelength side is included in the wavelength band of the G filter 15G. In other words, return light from the object irradiated by the light of the LED 16NRa is extracted mainly as components in the two wavelength bands of the R filter 15R and the G filter 15G.

When focusing on the LED 16NB and the LED 16NG, return lights of the respective LEDs 16NB and 16NG mainly have wavelengths corresponding to transmission wavelength bands of the B filter 15B and the G filter 15G in the color filter 15. When images of the return lights are simultaneously picked up, the return light can be substantially separated into two wavelength band components of the LED 16NB and the LED 16NG by a color separation operation explained below.

Therefore, as explained below, in the present embodiment, for example, when a narrowband light observation (abbreviated as NBI observation) is performed using lights in two narrowbands, a control circuit 31 performs illumination control to simultaneously irradiate the LED 16NB and the LED 16NG and perform image pickup by the image pickup device 14. Note that simultaneously causing LEDs in two or two or more wavelength bands to emit lights and simultaneously irradiating the lights in this way is also referred to as simultaneous irradiation mode or simultaneous illumination mode.

On the other hand, when the NBI observation is performed using lights in the three narrowbands of the LED 16NG, the LED 16NRa, and the LED 16NRb, as explained above, return light from the object irradiated by the light of the LED 16NRa is mainly extracted as components in the two wavelength bands of the R filter 15R and the G filter 15G. When images of the three return lights are simultaneously picked up, even if the color separation operation explained below is performed, the return light by the LED 16NRa cannot be substantially separated from the other two return lights. Therefore, the LED 16NG and the LED 16NRb and the LED 16NRa are irradiated in a time division manner and image pickup by the image pickup device 14 is performed. Irradiating LEDs in two or two or more wavelength bands respectively in a time division manner in this way is also referred to as time division illumination mode or time division illumination mode. Note that illumination lights irradiated in a time division manner are, for example, one illumination light like illumination light of the LED 16NRa (also referred to as NRa light) in some case and are two illumination lights like illumination light of the LED 16NG (also referred to as NG light) and illumination light of the LED 16NRb (also referred to as NRb light) in other cases.

Note that the control circuit 31 having a function of illumination control means performs the illumination control to simultaneously irradiate the LED 16NG and the LED 16NRb in a same manner as in a case of the LED 16NB and the LED 16NG and perform image pickup by the image pickup device 14.

A signal connector 10a provided at an end of a signal cable 10 extended from the operation portion 8 is detachably connected to the video processor 4.

As shown in FIG. 1, according to application of an image pickup device driving signal from the image pickup device driver 21 provided in the video processor 4, the image pickup device 14 outputs an image pickup signal or an image signal serving as a return light signal obtained by photoelectrically converting an optical image (by return light) formed on the image pickup surface 14a.

After being amplified by an amplifier 22, the image signal is subjected to pre-processing such as correlated double sampling processing in a pre-processing circuit 23. An output signal of the pre-processing circuit 23 is inputted to an A/D conversion circuit 24 and converted into a digital signal from an analog signal. R, G, and B signal components of an output signal of the A/D conversion circuit 24 are stored in an R memory 26R, a G memory 26G, and a B memory 26B, which configure a memory section 26, via a selector 25 changed over according to an array of R, G, and B filters of the color filter 15. In this case, in arrayed pixels serving as units of the color filter 15, the output signal is stored as R, G, and B signals of a same pixel in memory cells managed as a same address block.

An output signal from the memory section 26 is inputted to an image processing circuit 27 and, after being subjected to image processing such as color separation by a color separation circuit 27a configuring color separation operation means, inputted to D/A conversion circuits 28R, 28G, and 28B configuring a D/A conversion circuit section 28.

The color separation circuit 27a applies the color separation operation to a return light signal picked up by the image pickup means to separate the return light signal into independent image components in a plurality of predetermined wavelength bands (specifically, wavelength bands of R, G, and B) corresponding to transmission wavelength bands of a plurality of filters configuring the color filter 15 included in the image pickup means. Note that details of the color separation operation are explained below.

The output signal is converted into an analog image signal from a digital image signal by the D/A conversion circuits 28R, 28G, and 28B and outputted to channels of R, G, and B of the monitor 5. An image corresponding to an object image picked up by the image pickup device 14 is displayed on a display surface of the monitor 5 as an endoscopic image. Note that output signals of the D/A conversion circuits 28R, 28G, and 28B are recorded by the filing device 6 after being subjected to encoding for compression by an encoding circuit 29.

The video processor 4 includes a control circuit 31 that performs control of operations of the video processor 4 and the entire endoscope apparatus 1, a timing generator (abbreviated as TG) 32 that generates a timing signal for causing the video processor 4 to operate at predetermined timing, and a light-adjusting circuit 33.

The light-adjusting circuit 33 generates, from the output signal of the image processing circuit 27, a light adjustment signal for adjusting light to reference brightness and outputs the light-adjusting signal to the LED driving circuit 17. The light-adjusting circuit 33 adjusts, according to a light adjustment signal serving as a difference signal of the reference brightness, a light emission amount of the LED units 16, in other words, an illumination light amount of the object via the LED driving circuit 17 and performs light adjustment such that an image having the reference brightness is obtained.

For example, the operation portion 8 of the endoscope 2 is provided with a mode changeover switch 34 with which a user such as a surgeon performs changeover (or selection of one of) the WBI observation mode by normal light (white light) and the NBI observation mode and a scope ID memory 35 in which identification information (abbreviated as ID) peculiar to the endoscope 2 are stored.

The mode changeover switch 34 is provided with a selection switch 34a for, besides the changeover of the WBI observation mode and the NBI observation mode, selecting which narrowband light in a plurality of narrowbands (in the present embodiment, four narrowbands by the four LEDs 16NB, 16NG, 16NRa, and 16NRb) is used to perform the NBI observation in the NBI observation mode. Note that it may be defined that the mode changeover switch 34 performs changeover or selection of an observation mode including a selection function by the selection switch 34a.

When the user operates the mode changeover switch 34 to instruct changeover to one mode, a signal of the mode changeover instruction is inputted to the control circuit 31. The control circuit 31 has a function of a mode changeover control section 31a that performs a mode changeover control operation corresponding to the mode changeover instruction signal. Note that the mode changeover control section 31a also has a function of an NBI wavelength band selection control section that performs control for selecting an LED caused to emit light from the plurality of LEDs to perform the NBI observation in a wavelength band selected by the selection switch 34a.

The control circuit 31 has a function of a light adjustment parameter control section 31b that, when the light-adjusting circuit 33 generates the light adjustment signal, refers to an ID peculiar to the endoscope 2 and performs light adjustment parameter control according to a characteristic of the image pickup device 14 mounted on the endoscope 2 and transmission wavelength characteristics of the R, G, and B filters configuring the color filter 15 of the image pickup device 14.

In the present embodiment, the scope ID memory 35 configures an information storing section that stores information concerning the image pickup device 14 including the color filter 15 in the endoscope 2 including the scope ID memory 35 and at least information that can specify the transmission wavelength characteristics (transmission wavelength bands) of the R, G, and B filters configuring the color filter 15.

The control circuit 31 has a function of an illumination control section 31c that, when the endoscope 2 is connected to the video processor 4, reads out the ID as explained above and performs the illumination control by the LED units 16 in the light source device 3 according to the characteristic of the image pickup device 14 mounted on the endoscope 2, a characteristic of the color filter 15 of the image pickup device 14, and an observation mode instructed by the mode changeover switch 34 or the like.

When the illumination control section 31c performs illumination corresponding to the observation mode taking into account a transmission wavelength band of the color filter 15 of the image pickup device 14, the illumination control section 31c decides (determines) whether the illumination is performed in a simultaneous illumination system for simultaneously irradiating illumination lights of a plurality of wavelength bands or illumination is performed in a time division system for irradiating the illumination lights in the plurality of wavelength bands in a time division manner and performs the illumination control.

Specifically, in the present embodiment, the color filter 15 includes the R filter 15R. However, since a wavelength band of the R filter 15R includes wavelength bands of the two LEDs 16NRa and 16NRb in the narrow bands, when the two LEDs 16NRa and 16NRb simultaneously perform illumination, reflected lights or return lights of the respective LEDs cannot be separated by the R filter 15R.

Therefore, in the present embodiment, when the NBI observation is performed using the two LEDs 16NRa and 16NRb in the narrowbands for illumination lights, the illumination control section 31c of the control circuit 31 performs the illumination control to perform illumination of the two LEDs 16NRa and 16NRb in the narrowbands in a time division manner.

In a case of the LED 16G and the LED 16NRa in the narrowbands, since both wavelength bands are close to each other, it is difficult to sufficiently separate the wavelength bands with the G filter 15G and the R filter 15R. Therefore, when the NBI observation is performed using illumination lights of the LED 16G and the LED 16NRa, the illumination control section 31c of the control circuit 31 also performs the illumination control to perform illumination in a time division manner.

On the other hand, for example, when the NBI observation (image pickup) is performed using illumination lights of the LED 16NB and the LED 16NG in the narrowbands, return lights of the LED 16NB and the LED 16NG can be sufficiently color-separated by the B filter 15B and the G filter 15G. Therefore, when the illumination lights of the LED 16NB and the LED 16NG are used, the illumination control section 31c of the control circuit 31 performs the illumination control to simultaneously cause the LED 16NB and the LED 16NG to emit illumination lights and simultaneously irradiate the illumination lights on the object.

Note that, when the control circuit 31 performs the illumination control, the control circuit 31 also refers to a configuration and a light emission (illumination) characteristic of the LEDs of the LED units 16. For example, the LED driving circuit 17 outputs, to the control circuit 31, information concerning wavelength bands of lights emitted by the four LEDs 16NB, 16NG, 16NRa, and 16NRb functioning as the narrowband LEDs of the LED units 16. The control circuit 31 performs the illumination control after determining, referring to the information, whether illumination (irradiation) is performed in the simultaneous system or in a time division manner. Consequently, even when the endoscope apparatus 1 is configured using different kinds of the light source devices 3, measures can be appropriately taken.

Note that the illumination control section 31c of the control circuit 31 may play a function of, for example, a determining section (a deciding section) 31f. The LED driving circuit 17 does not limitedly input the information concerning the light emission wavelength of the LED units 16 to the control circuit 31. For example, an input section 36, which inputs information, provided in the video processor 4 may input, to the control circuit 31, information concerning the light emission wavelength band of the LED units 16 in the light source device 3 used together with the video processor 4. A light source control circuit, which controls an operation of the light source device 3, may be provided in the light source device 3. The light source control circuit may be configured to input the information concerning the light emission wavelength band of the LED units 16 to the control circuit 31. Note that, when the same light source device 3 is always used, it is unnecessary to refer to information concerning the light source device 3 every time an endoscopy is performed.

The control circuit 31 has a function of an image pickup control section (or an image pickup and signal processing control section) 31d that controls an image pickup operation by the image pickup device 14 and an operation of signal processing for an image pickup signal by the image pickup operation according to a characteristic of the image pickup device 14 mounted on the endoscope 2, a characteristic of the color filter 15 of the image pickup device 14, and an observation mode instructed by operation of the mode changeover switch 34. The control circuit 31 also has a function of a readout control section 31e that performs readout control to continuously read out return light signals within one frame period with the image pickup device 14 when simultaneous illumination is performed and perform readout for a predetermined period within the one frame period with the image pickup device 14 when time division illumination is performed. Note that FIG. 8 and FIG. 9 referred to below are representative examples of this operation.

The control circuit 31 has a function of the determining section (or the deciding section) 31f for performing illumination control and image pickup control corresponding to the observation mode in order to perform a control operation of the illumination control section 31c or the like. The video processor 4 includes a memory 37 functioning as an illumination information storing section in which information for performing illumination and image pickup corresponding to the observation mode is stored by the determining section 31. Note that the memory 37 is configured by a nonvolatile and rewritable recording medium such as a flash memory.

For example, in a state of initial setting, the control circuit 31 stores, in the memory 37, information for performing the simultaneous illumination or the time division illumination corresponding to observation modes from information concerning (the image pickup device 14 including the color filter 15 of) the endoscope 2 connected to the video processor 4 and information concerning the LED units 16 of the light source device 3 to which the endoscope is connected to be used and information in a case in which control of a corresponding image pickup operation or the like is performed using the image pickup device 14. When an observation mode is actually instructed (designated), the control circuit 31 reads out corresponding information from the memory 37 and performs control of illumination and image pickup.

Note that the control circuit 31 includes the mode changeover control section 31a, the light adjustment parameter control section 31b, the illumination control section 31c, the image pickup control section 31d, the readout control section 31e, and the determining section 31f. However, an electronic circuit or the like having the functions of the mode changeover control section 31a to the determining section 31f may be provided on an outside of the control circuit 31. The control circuit 31 and the mode changeover control section 31a to the determining section 31f may be configured using a central processing unit (CPU) or may be configured using a dedicated electronic circuit, an FPGA (Field Programmable Gate Array), or the like.

Figure 4:
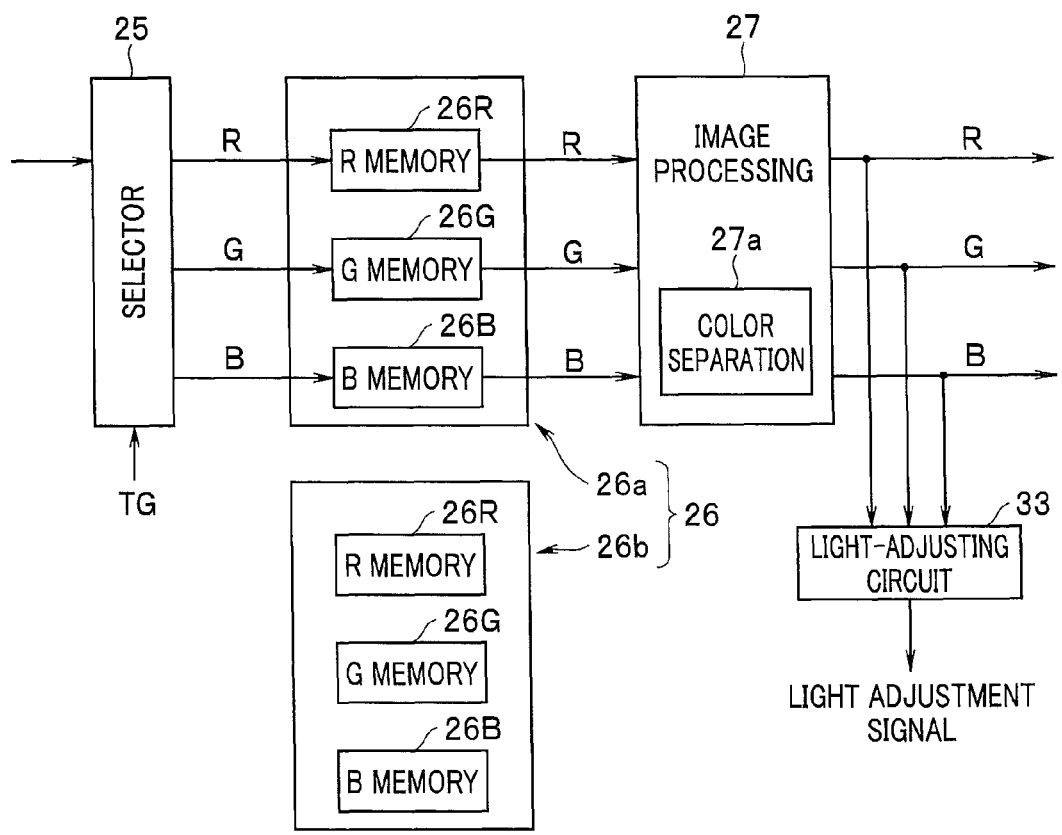
FIG. 4 is a block diagram showing a configuration example of a memory section peripheral section.

FIG. 4 shows a configuration of a peripheral section of the memory section 26 that stores component signals of R, G, and B in the WBI observation mode or the like. In the present embodiment, the memory section 26 includes a first memory group 26a and a second memory group 26b. Note that the second memory group 26b does not have to be used in the WBI observation mode in which image pickup is performed under white light. In the NBI observation mode explained below, the second memory group 26b is sometimes used.

The control circuit 31 controls changeover of the selector 25 via, for example, the TG 32 to change an output signal of the image pickup device 14 to component signals of R, G, and B in pixel units and stores the component signals in R, G, and B memories 26R, 26G, and 26B of one memory group 26a configuring the memory section 26.

After storing the component signals of R, G, and B in the first memory group 26a for one frame, the control circuit 31 simultaneously reads out the component signals and, after subjecting the component signals to contour emphasis or the like in the image processing circuit 27, outputs the component signals to the light-adjusting circuit 33 and a post stage side. The light-adjusting circuit 33 generates a light adjustment signal from the component signals of R, G, and B, outputs the light adjustment signal to the light source device 3 side, and adjusts a light emission amount of the white LED 16W via the LED driving circuit 17 to be reference brightness. An image of the object is displayed in color on the monitor 5 according to image signals of R, G, and B.

In the case of the configuration shown in FIG. 4, the output signal is changed to the component signals of R, G, and B according to the changeover of the selector 25. However, the output signal may be separated into image signals of R, G, and B, which more faithfully reflect a wavelength characteristic of return light, by using the color separation circuit 27a in the image processing circuit 27.

In the NBI observation mode in the present embodiment, lights in a plurality of narrowbands having different wavelengths are irradiated to pick up an image of return light. However, images of signals of RGB actually picked up through the color filter include not only return lights in transmission bands of the respective filters but also wavelength band components of return lights corresponding to the filters of the different colors. This is because the color filter of the image pickup device actually has a certain degree of transmittance with respect to wavelength bands other than the bands of the colors of RGB. A state in which components of a plurality of return lights having different wavelength bands is included in one image signal is referred to as color mixture.

In the present embodiment, in particular, in the NBI observation mode, an operation of color separation for separating mixed-color RGB signals into independent wavelength components is performed using a matrix circuit, which performs matrix conversion, configuring the color separation circuit 27a.

In a case of the NBI observation mode, when a matrix M for performing the color separation operation is integrated with respect to component signals I of R, G, and B inputted to the image processing circuit 27 from the image pickup device 14 through the selector 25 in the video processor 4, the matrix M configuring the matrix conversion circuit is set as described below to obtain a unit matrix S.

$$M \cdot I = S \tag{1}$$

For example, when it is desired to separate images of component signals of R, G, and B picked up by the image pickup device 14 under illumination lights in three wavelength bands and inputted through the selector 25 into light components of three bands, the following Expression (2) is obtained:

$$\begin{pmatrix} M_{11} & M_{12} & M_{13} \\ M_{21} & M_{22} & M_{23} \\ M_{13} & M_{23} & M_{33} \end{pmatrix} \cdot \begin{pmatrix} I_{R,\lambda 1} & I_{R,\lambda 2} & I_{R,\lambda 3} \\ I_{G,\lambda 1} & I_{G,\lambda 2} & I_{G,\lambda 3} \\ I_{B,\lambda 1} & I_{B,\lambda 2} & I_{B,\lambda 3} \end{pmatrix} = \begin{pmatrix} 1 & 0 & 0 \\ 0 & 1 & 0 \\ 0 & 0 & 1 \end{pmatrix} \tag{2}$$

Note that Mij (i, j=1, 2, 3) in Expression (2) indicates a matrix coefficient. $I_{J, \lambda i}$ indicates a signal component of a wavelength λi obtained when J filters with J (=R, G, B) are used.

Figure 5A:
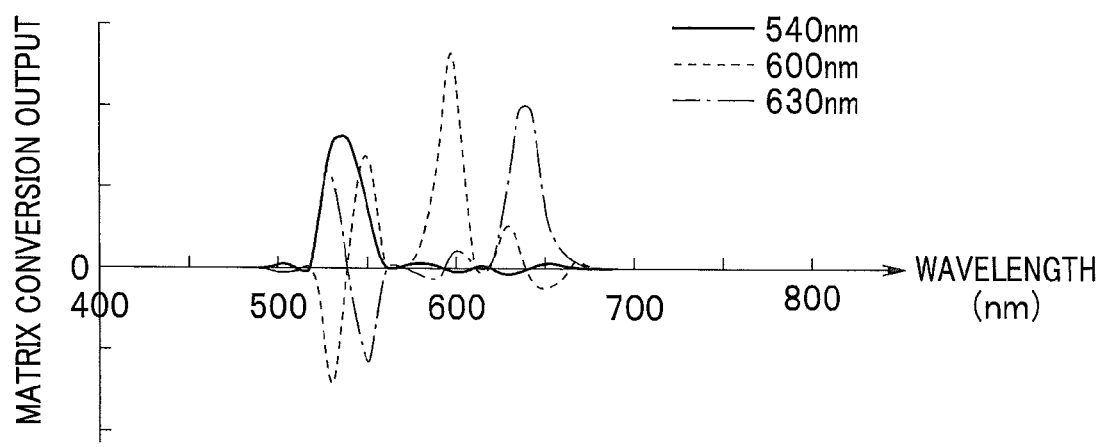
FIG. 5A is a diagram showing a spectral characteristic example in a case in which a color separation operation for return light is performed in a state in which illumination lights in two wavelength bands are included in one transmission wavelength band.

In Expression (2), it looks as if a signal after matrix application is separated into a component for each band. However, when the illumination lights in the three wavelength bands are, for example, lights in narrow bands of three bands having wavelengths of 540 nm, 600 nm, and 630 nm, if it is attempted to separate return lights of the lights, distortion occurs in an unintended wavelength band as shown in FIG. 5A.

This is because both of return lights from the object in a case of illumination lights of 600 nm and 630 nm have nearly maximum sensitivity in a transmission wavelength band of the R filter 15R. Therefore, in this case, color separation cannot be effectively performed under simultaneous illumination of the lights of 600 nm and 630 nm.

Therefore, for example, only the light of 600 nm is irradiated in a time division manner at timing different from the other lights (540 nm and 630 nm) and an image of the light is picked up. Then, the return lights of the respective lights can be separated and images of the return lights are picked up.

In this case, the lights in the two bands of 540 nm and 630 nm are simultaneously irradiated. Therefore, an arithmetic expression of the color separation is as indicated by Expression (3).

$$\begin{pmatrix} M_{11} & M_{12} & M_{13} \\ M_{21} & M_{22} & M_{23} \end{pmatrix} \cdot \begin{pmatrix} I_{R,\lambda 1} & I_{R,\lambda 2} \\ I_{G,\lambda 1} & I_{G,\lambda 2} \\ I_{B,\lambda 1} & I_{B,\lambda 2} \end{pmatrix} = \begin{pmatrix} 1 & 0 \\ 0 & 1 \end{pmatrix} \quad (3)$$

The matrix M in this case is an asymmetrical matrix of two rows and three columns. Therefore, an expression for calculating the matrix coefficient can be obtained using a pseudo inverse matrix $I^+$ of the signal I as indicated by the following Expression (4):

$$M = S \cdot I^+ \quad (4)$$

Figure 5B:
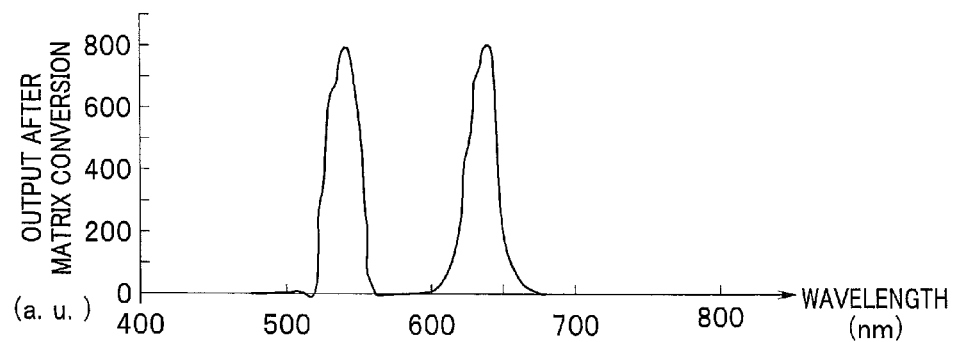
FIG. 5B is a diagram showing a spectral characteristic example in a case in which the color separation operation for the return light is performed in a state in which illumination light in one wavelength band is included in each of two different transmission wavelength bands.
Figure 5C:
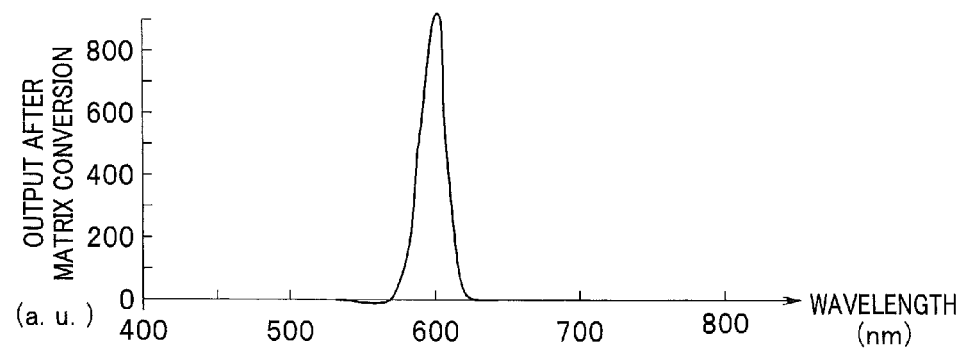
FIG. 5C is a diagram showing a spectral characteristic example in a case in which the color separation operation for the return light is performed in a state in which illumination light in one wavelength band is included in one transmission wavelength band.

A graph of a spectral characteristic of a signal subjected to color separation by the color separation operation of Expression (3) is shown in FIG. 5B. As shown in FIG. 5B, it is seen that, when the illumination lights having the narrowband wavelengths of 540 mm and 630 mm are simultaneously irradiated, return lights of the illumination lights can be sufficiently separated. FIG. 5C shows a spectral characteristic of an output signal after matrix conversion in a case in which, when only the illumination light having the narrowband wavelength of 600 nm is irradiated in independent time, an image of return light of the illumination light is picked up. In this case, the problem of the color mixture does not occur.

In this way, in the present embodiment, illumination (and image pickup) is controlled to perform the simultaneous illumination in a case of illumination lights in a plurality of wavelength bands corresponding to a case in which color separation can be sufficiently performed in the color separation circuit 27a and perform illumination in a time division manner in a case of illumination lights in a plurality of wavelength bands corresponding to a case in which the color separation cannot be sufficiently performed.

FIG. 6 shows an explanatory diagram of an overall operation in the present embodiment. FIG. 6(A) shows spectral characteristics of the R, G, and B filters of the color filter 15 shown in FIG. 3(A). FIG. 6(B) shows a characteristic of light intensity in a case in which the LEDs 16NB and 16NG shown in FIG. 3(B) are caused to emit light. In the figures, the LEDs 16NB and 16NG are simplified and indicated by NB and NG. A characteristic example of signal intensity in a case in which image pickup is performed by the image pickup device 14 under simultaneous illumination of both the LEDs 16NB and 16NG is shown in FIG. 6(C).

In this case, a characteristic example of signal intensity in a case in which the color separation operation is performed by the color separation circuit 27a is as shown in FIG. 6(D). A sufficiently color-separated image signal is obtained.

On the other hand, when image pickup in the LEDs 16NG, 16NRa, and 16NRb different from the LEDs in FIG. 6(B) and having characteristics of light intensity shown in FIG. 6(E) is performed using the color filter 15 shown in FIG. 6(A), in a state in which the LEDs are simultaneously illuminated, a characteristic example of signal intensity in a case in which image pickup is performed by the image pickup device 14 is as shown in FIG. 6(F).

In this case, for example, signal intensity by the R filter 15R has a small difference value with respect to NRa light and NRb light. Therefore, color separation is insufficient as explained with reference to FIG. 5A and the like (this state is indicated by color mixture occurrence in FIG. 6(G)). Therefore, in the present embodiment, illumination is performed in a time division manner in a case of illumination light in FIG. 6(E).

The endoscope apparatus 1 having such a configuration includes the LED units 16 (the light guide 9 and the illumination lens 12) functioning as illuminating means capable of irradiating white light and illumination light formed by lights in a plurality of different wavelength bands on a subject, the image pickup device 14 functioning as image pickup means including the color filter 15 configured by the plurality of filters 15R, 15G, and 15B that respectively transmit lights in a plurality of different wavelength bands, the image pickup device 14 subjecting return light from the subject to image pickup on the basis of irradiation of the illumination light by the illuminating means, and the illumination control section 31c functioning as illumination control means for, when image pickup is performed by the image pickup means using the plurality of filters 15R, 15G, and 15B, with respect to a transmission wavelength band of at least one filter 15R in the plurality of filters 15R, 15G, and 15B, performing control to time-divide the illumination light irradiated by the illuminating means (as a specific example, the LEDs 16NRa and 16NRb) into two or more and irradiate the illumination light when images of at least two or more return lights included in the transmission wavelength band are picked up and, when image pickup is performed by the image pickup means using the plurality of filters 15R, 15G, and 15B, in a state in which one or less return light is included in each of transmission wavelength bands of at least two or more filters 15G and 15B in the plurality of filters, when images of two or more return lights are picked up, performing control to simultaneously irradiate illumination lights in two or more wavelength bands (as a specific example, the LEDs 16NG and 16NB) irradiated by the illuminating means to correspond to the two or more return lights. Note that, in the present embodiment, the configuration is shown in which the image pickup device including the primary color filters of RGB is used. However, same applies to a complementary color image sensor including complementary color filters of Mg+Cy, G+Ye, G+Cy, Mg+Ye, and the like. In this case, for example, the j component of the matrix in Expression (2) and Expression (3) includes components of 1 to 4. The RGB components in the signal I are represented as the four kinds of filter components.

Figure 7:
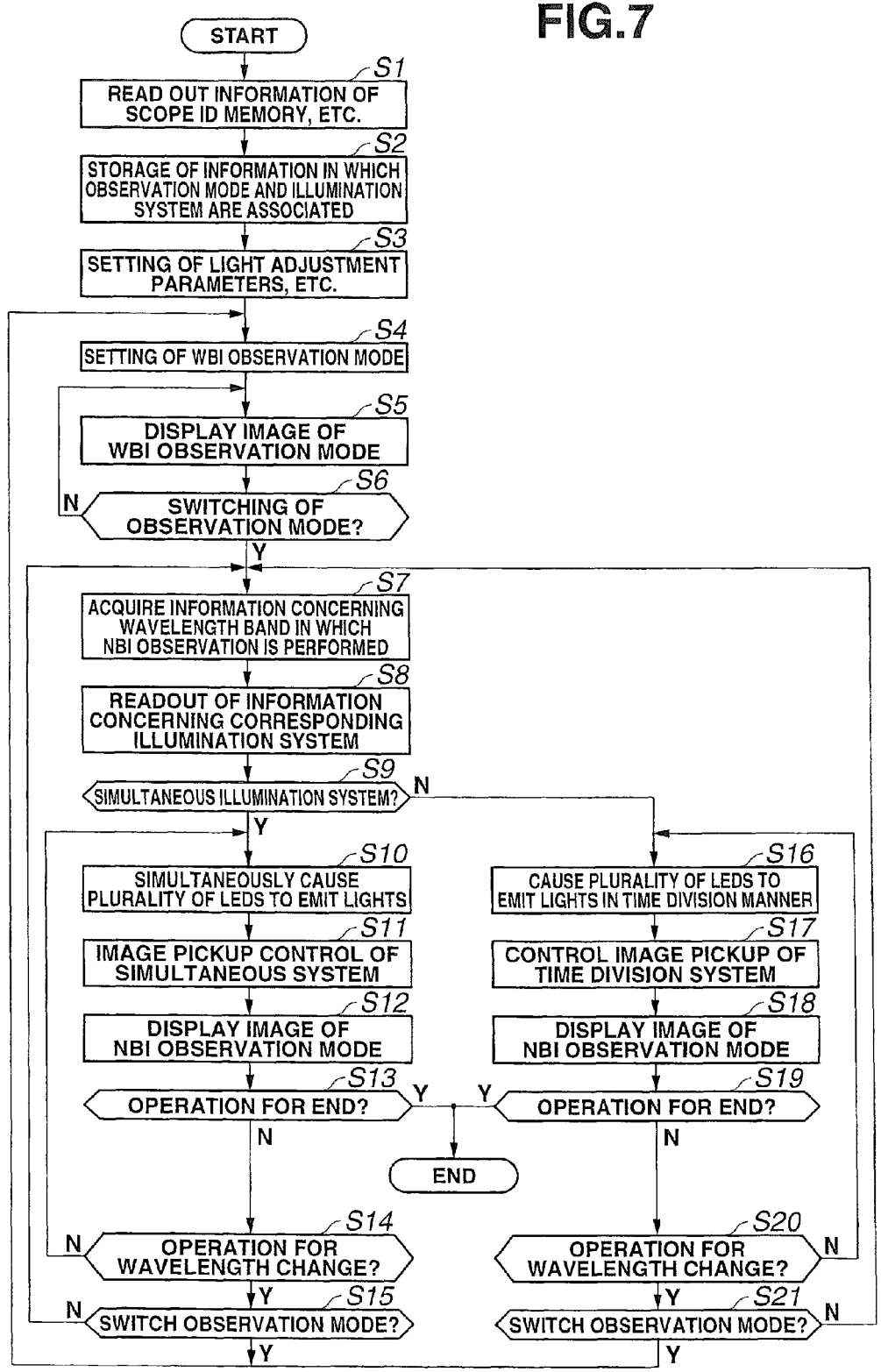
FIG. 7 is a flowchart showing an overall operation content of the first embodiment.

An operation in the present embodiment is explained. FIG. 7 shows a representative operation content in the present embodiment. As shown in FIG. 1, the light guide connector 9a and the signal connector 10a of the endoscope 2 are connected to the light source device 3 and the video processor 4 and power supplies of the light source device 3 and the video processor 4 are turned on to change the endoscope apparatus 1 to an operation stage. In first step S1, the control circuit 31 reads out information concerning the connected endoscope 2 from the scope ID memory 35.

The control circuit 31 reads out information concerning light emission wavelength characteristics of the plurality of LEDs configuring the LED units 16 of the light source device 3 (from the LED driving circuit 17, etc.).

In step S2, from information concerning a transmission wavelength characteristic of the color filter 15 mounted on the endoscope 2 and information concerning a light emission wavelength band of the LEDs configuring the LED units 16 of the light source device 3, the determining section 31f of the control circuit 31 performs decision concerning whether simultaneous illumination is possible when illumination and image pickup corresponding to a plurality of observation modes are performed. The determining section 31f stores, in the memory 37, information concerning an observation mode in which the simultaneous illumination is possible and information concerning an observation mode in which it is necessary to illuminate the LEDs in a time division manner.

In other words, the determining section 31f stores, in the memory 37, information in which illumination systems (illumination modes) are associated with the respective observation modes.

In step S3, the control circuit 31 performs setting of a light adjustment parameter and the like according to a characteristic and the like of the image pickup device 14. In step S3, the control circuit 31 further performs adjustment of a white balance. When processing for initial setting ends in this way, in step S4, the control circuit 31 sets the WBI observation mode. In step S4, the control circuit 31 causes only the white LED 16W of the LED units 16 of the light source device 3 to emit light and sets a state in which the object is illuminated by white light. The control circuit 31 performs control to perform image pickup of a simultaneous type using the color filter 15 under irradiation of illumination of white light.

According to the image pickup of the simultaneous type, a color image in the WBI observation mode is displayed on the monitor 5 as explained below.

In this case, the image pickup device 14 including the color filter 15 outputs image signals of R, G, and B obtained by color-separating return light from the object under the irradiation of the white light into R, G, and B lights with the R, G, and B filters 15R, 15G, and 15B. After being processed through the amplifier 22, the pre-processing, and A/C conversion, and the like, the image signals of R, G, and B are stored in the memory section 26 through the selector 25.

In this case, the selector 25 is changed over in pixel units. Component signals of R, G, and B are stored in the R, G, and B memories 26R, 26G, and 26B of the memory section 26 (one memory group 26a). After being stored in the first memory group 26a for one frame, the component signals are simultaneously read out. After being subjected to contour emphasis or the like in the image processing circuit 27, image signals of R, G, and B are outputted to the light-adjusting circuit 33 and a post stage side. The light-adjusting circuit 33 generates a light adjustment signal from the image signals of R, G, and B, outputs the light adjustment signal to the light source device 3 side, and adjusts a light emission amount of the white LED 16W via the LED driving circuit 17 to be reference brightness. An image of the object is displayed in color on the monitor 5 according to the image signals of R, G, and B.

In step S6 in FIG. 7, the control circuit 31 monitors whether changeover from the WBI observation mode to the NBI observation mode is performed by the mode changeover switch 34. When the changeover is not performed, the control circuit 31 returns the processing to the processing in step S5.

The surgeon observes an affected part or the like in the WBI observation mode. When the surgeon desires to observe a traveling state of a blood vessel near a surface layer of the affected part more in detail, the surgeon operates the mode changeover switch 34 and changes over the WBI observation mode to the NBI observation mode.

In the present embodiment, when the surgeon changes over the WBI observation mode to the NBI observation mode, the surgeon further performs selection concerning illumination light in which wavelength band in illumination lights in a plurality of wavelength bands is used to perform the NBI observation. When the selection is not performed by the surgeon, the control circuit 31 may perform display for urging the selection. Alternatively, when the selection is not performed within a predetermined time, the control circuit 31 may perform setting to use illumination light in a standard wavelength band set in default.

When the changeover from the WBI observation mode to the NBI observation mode is performed in step S6, in the next step S7, the control circuit 31 acquires information concerning a wavelength band in which the NBI observation is performed selected by the surgeon or the like using the selection switch 34a.

Further, in the next step S8, the control circuit 31 reads out information concerning an illumination system corresponding to the information from the memory 37.

In the next step S9, the control circuit 31 determines, according to the information read out from the memory 37, whether the illumination system corresponds to a simultaneous illumination system.

In a case of a decision result indicating that the illumination system corresponds to the simultaneous illumination system, in step S10, the illumination control section 31c of the control circuit 31 performs control to simultaneously cause a plurality of LEDs corresponding to the selected NBI observation mode to emit light via the LED driving circuit 17 and perform the simultaneous illumination.

In step S11, the image pickup control section 31d of the control circuit 31 controls the respective sections of the video processor 4 to perform an image pickup operation corresponding to the simultaneous illumination. As shown in step S12, an image in the NBI observation mode picked up in the simultaneous illumination system is displayed on the monitor 5.

In the next step S13, the control circuit 31 determines, for example, whether instruction operation for ending an endoscopy is performed from the input section 36 and, when the instruction operation for ending the endoscopy is performed, the control circuit 31 ends the processing shown in FIG. 7.

On the other hand, when the instruction operation for ending the endoscopy is not performed, in the next step S14, the control circuit 31 determines whether the surgeon performs changing operation for a wavelength band in the NBI observation mode with the selection switch 34a.

In a case of a decision result indicating that the changing operation is not performed, processing returns to processing in step S10 and same processing is continued. On the other hand, when the operation for the wavelength change is performed, in step S15, the control circuit 31 further determines whether a changeover operation from the NBI observation mode to the WBI observation mode is performed by the mode changeover switch 34.

In a case of a decision result indicating that only the operation for wavelength change is performed rather than changeover to the WBI observation mode by the mode changeover switch 34, the processing returns to processing in step S7. On the other hand, in a case of a decision result indicating that the NBI observation mode is changed over to the WBI observation mode, the processing returns to processing in step S4. The WBI observation mode is set and the processing explained above is repeated.

On the other hand, in a case of a decision result indicating that the illumination system corresponds to a time division illumination system rather than the simultaneous illumination system in step S9, in step S16, the illumination control section 31c of the control circuit 31 performs control to cause a plurality of LEDs corresponding to the selected NBI observation mode to emit light in a time division manner via the LED driving circuit 17 and perform the time division illumination.

In step S17, the image pickup control section 31d of the control circuit 31 controls the respective sections of the video processor 4 to perform an image pickup operation corresponding to the time division illumination. As shown in step S18, an image of the NBI observation mode picked up in the time division illumination system is displayed on the monitor 5 as shown in step S18.

In the next step S19, the control circuit 31 determines, for example, whether instruction operation for ending the endoscopy is performed from the input section 36. When the instruction operation for ending the endoscopy is performed, the control circuit 31 ends the processing shown in FIG. 7.

When the instruction operation for the end is not performed in step S19, in the next step S20, the control circuit 31 determines whether the surgeon performs change operation for a wavelength band in the NBI observation mode with the selection switch 34a. In a case of a decision result indicating that the changing operation is not performed, the processing returns to processing in step S16 and the same processing is continued.

On the other hand, when the operation for the wavelength change is performed, further, in step S21, the control circuit 31 determines whether changeover operation from the NBI observation mode to the WBI observation mode is performed by the mode changeover switch 34. In a case of a decision result indicating only the operation for the wavelength change rather than the changeover to the WBI observation mode by the mode changeover switch 34, the processing returns to the processing in step S7. On the other hand, in a case of a decision result indicating the changeover operation to the WBI observation mode, the processing returns to the processing in step S4. The WBI observation mode is set and the processing explained above is repeated.

Figure 8:
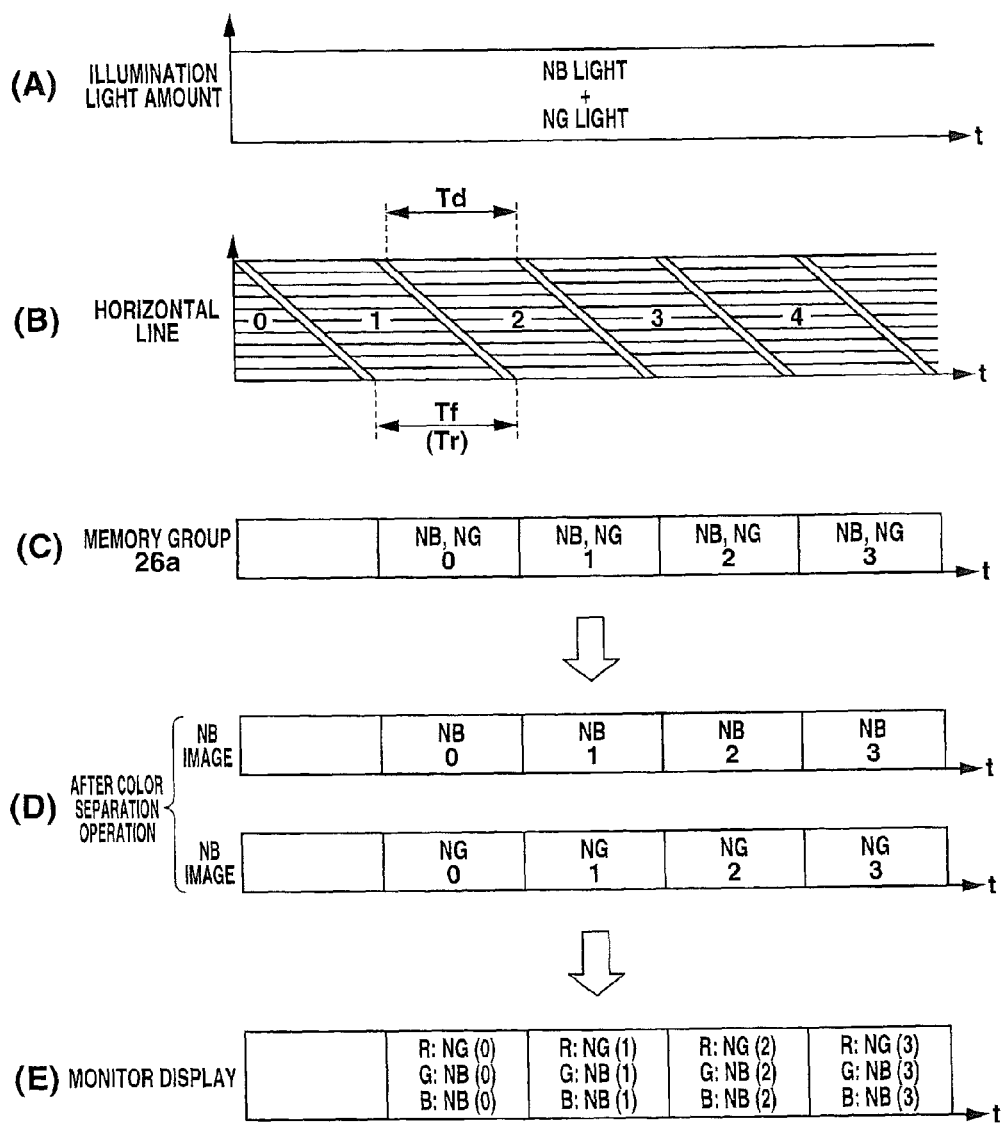
FIG. 8 is an explanatory diagram of an operation in a case in which image pickup is performed in a state of a simultaneous illumination system.

Next, an operation in a case of the simultaneous illumination system is explained. FIG. 8 shows an operation in the NBI observation mode in a case in which the LEDs 16NB and 16NG are used. Note that, in the following explanation, a CMOS sensor is used as the image pickup device 14. Note that each of lateral axes in FIG. 8 indicates time t. In this case, the illumination control section 31c of the control section 31 controls the LEDs 16NB and 16NG of the LED units 16 configuring the illuminating means to simultaneously irradiate illumination lights in two wavelength bands. An image of a return light signal picked up by the image pickup device 14 is continuously read out within one frame period.

In this case, as shown in FIG. 8(A), light of the LED 16NB and light of the LED 16NG (abbreviated as NG light+NG light) serving as illumination lights simultaneously emitted by the LEDs 16NB and 16NG are obtained as shown in FIG. 8(A). Under the simultaneous illumination, a state of readout in a case in which a CMOS sensor is used as the image pickup device 14 is as shown in FIG. 8(B).

In FIG. 8(B), readout is sequentially performed in respective horizontal line directions of the CMOS sensor. A period indicated by a horizontal line in FIG. 8(B) is an illumination period (an exposure period) Td in which illumination is performed to acquire an image for one frame. A period short in a horizontal direction indicated by two oblique lines following the exposure period Td is a readout period for one horizontal line. A period in which the entire horizontal line (i.e., the image for one frame) is read out is a readout period Tr. In a case of FIG. 8(B), the readout period Tr coincides with one frame period Tf in which the image for one frame is acquired.

In this case, image pickup is performed in a continuous readout (rolling shutter) system not including a non-readout period in which readout is not performed.

In a case of FIG. 8, since continuous readout not including the non-readout period is performed, it is possible to perform image pickup and image display at a high frame rate.

For example, when the one frame period (readout period) Tf is 1/60 sec, band images of the NB light and the NG light are updated all together at a frame rate of 60 P (progressive). Note that 0, 1, 2, 3, and 4 in respective frame periods Tf in FIG. 8(B) respectively indicate zero-th, first, second, third, and fourth frames. 0, 1, and the like in FIG. 8(C), FIG. 8(D), and FIG. 8(E) also indicate images of frames corresponding thereto. The same applies in FIG. 9, FIG. 12, and the like referred to below.

FIG. 8(C) shows a state in which an NB image acquired under the NB light and an NG image acquired under the NG light are stored in one memory group 26a of the memory section 26.

FIG. 8(D) shows the NB image and the NG image after the color separation operation by the color separation circuit 27a.

FIG. 8(E) shows a display example in which the NB image and the NG image after the color separation operation by the color separation circuit 27a are displayed on the monitor 5. In the present embodiment, the NG image (of the NG light), the NB image (of the NB light), and the NB image are respectively inputted to R, G, and B channels of the monitor 5 to be displayed in color. Note that, for example, R:NG(0) in FIG. 8(E) indicates that the NG image of the R channel is a 0-th frame.

Figure 9:
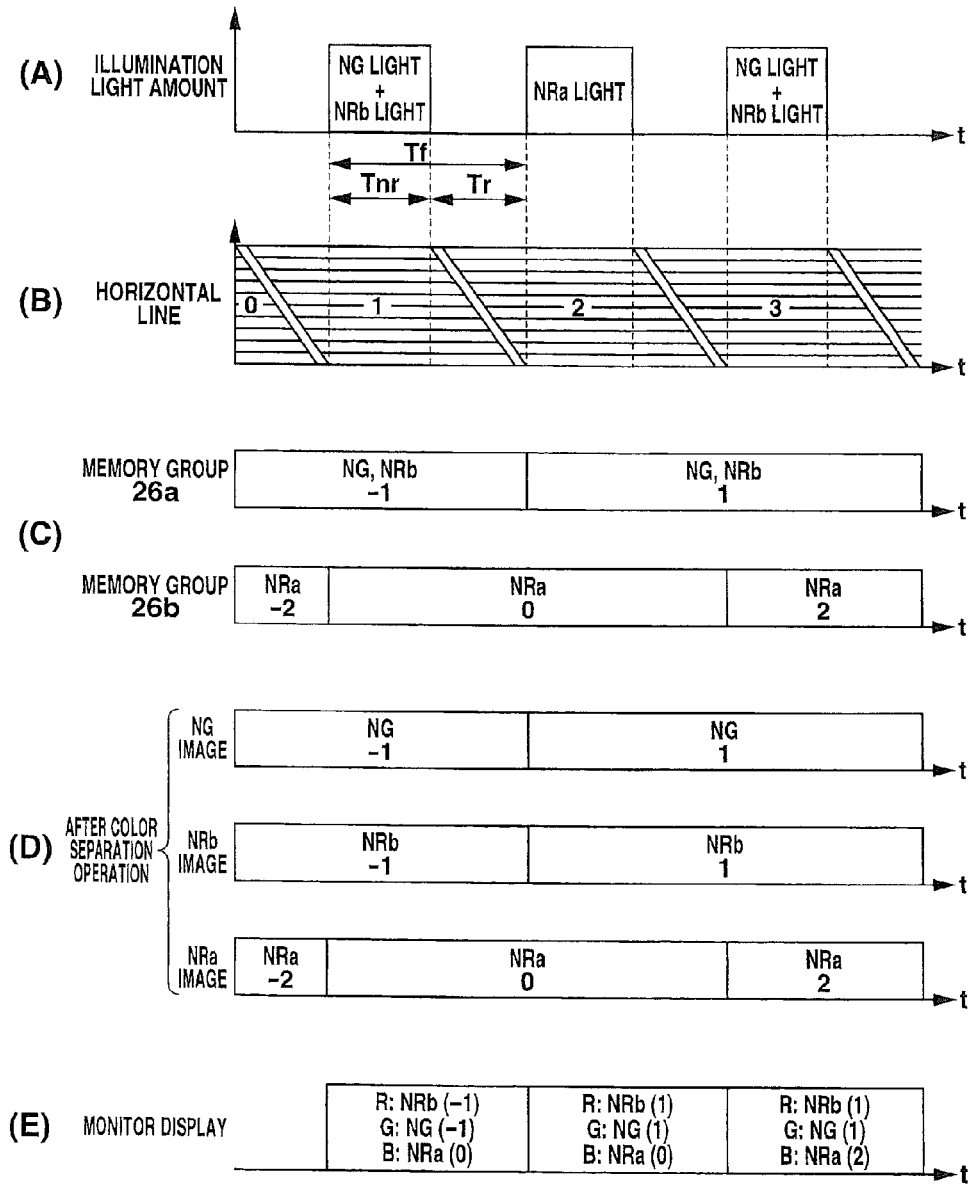
FIG. 9 is an explanatory diagram of an operation in a case in which image pickup is performed in a state of a time division system.

FIG. 9 shows an operation in a case of an illumination system in which the simultaneous illumination and the time division explained with reference to FIG. 5B and FIG. 5C are combined. In this case, as shown in FIG. 9(A), readout is performed in a time division manner in a period in which the NG light and the NRb light are simultaneously irradiated (illuminated) and a period in which only the NRa light is irradiated. A non-readout period Tnr in which readout is not performed is also provided.

In this case, a sum of the non-readout period Tnr and the readout period Tr in which readout is performed is the one frame period Tf. For example, in the non-readout period Tnr in a first frame (1 in FIG. 9(B)), simultaneous illumination of the NG light and the NRb light is performed. After this period, there is the readout period Tr in which readout of the CMOS sensor is performed. Illumination light is irradiated during the non-readout period Tnr other than the readout period Tr, which is a predetermined period in the one frame period Tf. In a case of FIG. 9, the period in which the illumination light is irradiated is set the same as the non-readout period Tnr.

After the readout period Tr, illumination of the NRa light in a second frame (2 in FIG. 9(B)) is performed. After this period, there is the readout period Tr in which readout of the CMOS sensor is performed. After the readout period Tr, simultaneous illumination of the NG light and the NRb light in a third frame (3 in FIG. 9(B)) is performed. After this period, there is the readout period Tr in which readout of the CMOS sensor is performed. Such time-division (intermittent) illumination and image pickup are repeated.

In this case, as shown in FIG. 9(C), an image signal picked up under simultaneous illumination of the NG light and the NRb light is stored in the memory group 26a and an image signal picked up under illumination of the NRa light is stored in the memory group 26b. Note that, for example, −1 in HG and NRb and −2 in NRa respectively indicate an immediately preceding frame of the 0-th frame and a second immediately preceding frame of the 0-th frame.

The image of the image signal picked up under the simultaneous illumination of the NG light and the NRb light is subjected to the color separation operation by the color separation circuit 27a functioning as color separation operation means as shown in FIG. 9(D) and separated into an NG image and an NRb image.

As shown in FIG. 9(E), color-separated image signal components are inputted to the R, G, and B channels of the monitor 5. An NBI image picked up under narrowband illumination of NG, Nra, and Nrb is displayed in pseudo color.

In this case, when the readout period Tr of all pixel readout of the CMOS sensor is set to 1/60 sec as in the case of FIG. 8, if the non-readout period Tnr is set to same 1/60 sec, the one frame period Tf is 1/30 sec. An image of (Ng, NRb) and an image of NRa are alternately acquired at a frame rate of 30 P.

In an example shown in FIG. 9(E), the alternately-acquired both images are displayed in pseudo color. Note that, when compared with the case of FIG. 8, the frame rate is low. Therefore, in the case of FIG. 9, pixel binning for performing pixel addition of the CMOS sensor may be performed in association with changeover from a mode in FIG. 8 to a mode in FIG. 9 to reduce, with the pixel addition, a number of pixels, images of which are picked up, and improve sensitivity through the pixel addition.

For example, it is possible to perform display at 60 P by setting the readout period Tr to 1/120 sec and setting the non-readout period Tnr to 1/120 sec.

According to the present embodiment in which the above operation is performed, it is possible to provide the endoscope apparatus 1 that can appropriately perform illumination control (illumination in the simultaneous system or illumination in the time division system) corresponding to a transmission wavelength characteristic of the color filter 15 included in the image pickup device 14 configuring image pickup means.

That is, illumination lights in a different plurality of wavelength bands required to be actually irradiated when the endoscopy is performed (according to selection by the surgeon or the like) is controlled according to the transmission wavelength characteristics of the R, G, and B filters 15R, 15G, and 15B of the color filter 15 of the image pickup device 14 such that a color-separated image can be surely acquired by performing the illumination in the simultaneous system in a case of illumination lights of a plurality of wavelength bands in a case in which returns lights can be sufficiently color-separated by the color filter 15 and performing the illumination of the time division system in a case of illumination lights in a plurality of wavelength bands in a case in which return lights cannot be color-separated by the color filter 15. Therefore, the surgeon can smoothly perform the endoscopy.

According to the present embodiment, the driving of the image pickup device 14 and the signal processing for the output signal of the image pickup device 14 are performed according to the illumination in the simultaneous system and the illumination in the time division system. Therefore, it is possible to provide the endoscope apparatus 1 having high convenience.

As a first modification of the present embodiment, a case is explained in which the NBI observation is performed using LEDs 16NBa and 16NBb that emit lights in two narrowbands in a wavelength band of the B filter 15B, LEDs 16NGa and 16NGb that emit lights in two narrow bands in a wavelength band of the G filter 15G, and LEDs 16NRa and 16NRb that emit lights in two narrow bands in a wavelength band of the R filter 15R.

As it is understood from the above explanation, the respective filters of the color filter 15 of the image pickup device 14 (more specifically, the CMOS sensor) cannot separate return lights in two narrowband lights. Therefore, time-division illumination and image pickup are performed in a combination in which color separation can be performed.

Specifically, the LEDs are divided into the LED 16NBa, the LED 16NGa, and the LED 16NRb and the LED 16NBb, the LED 16NGb, and the LED 16NRb and illumination and image pickup are performed in a time division manner.

When the illumination and the image pickup are performed in a time division manner in this way, one narrowband light is included in each of the respective filters. Therefore, it is possible to acquire an NBI image sufficiently color-separated and picked up under illumination lights of respective narrowband lights.

In this case, six images can be acquired: an NBa image, an NGa image, and an NRa image under illumination of the LED 16NBa, the LED 16NGa, and the LED 16NRb and an NBb image, an NGb image, and an NRb image under illumination of the LED 16NBb, the LED 16NGb, and the LED 16NRb. Therefore, the surgeon can also select, for example, from the input section 36, an image to be displayed on the monitor 5 and cause the monitor 5 to display the image. For example, images of NRa, NGb, and NBa may be inputted to the R, G, and B channels of the monitor 5 and displayed in color. In this case, images other than such display can also be displayed.

It is also possible that the display surface of the monitor 5 is set in, for example, a two-screen display mode for arranging two endoscopic images on left and right and displaying the endoscopic images, and, for example, images of NRa, NGb, and NBa are displayed in color on one screen and images of NRb, NGa, and NBb are displayed in color on the other screen.

It is also possible that two monitors 5 are set and the images of NRa, NGb, and NBa are displayed in color on one monitor and the images of NRb, NGa, and NBb are displayed in color on the other monitor.

According to this modification, when the NBI observation is performed, it is possible to perform display of the NBI image further meeting a demand of the surgeon.

Second Embodiment

Figure 10:
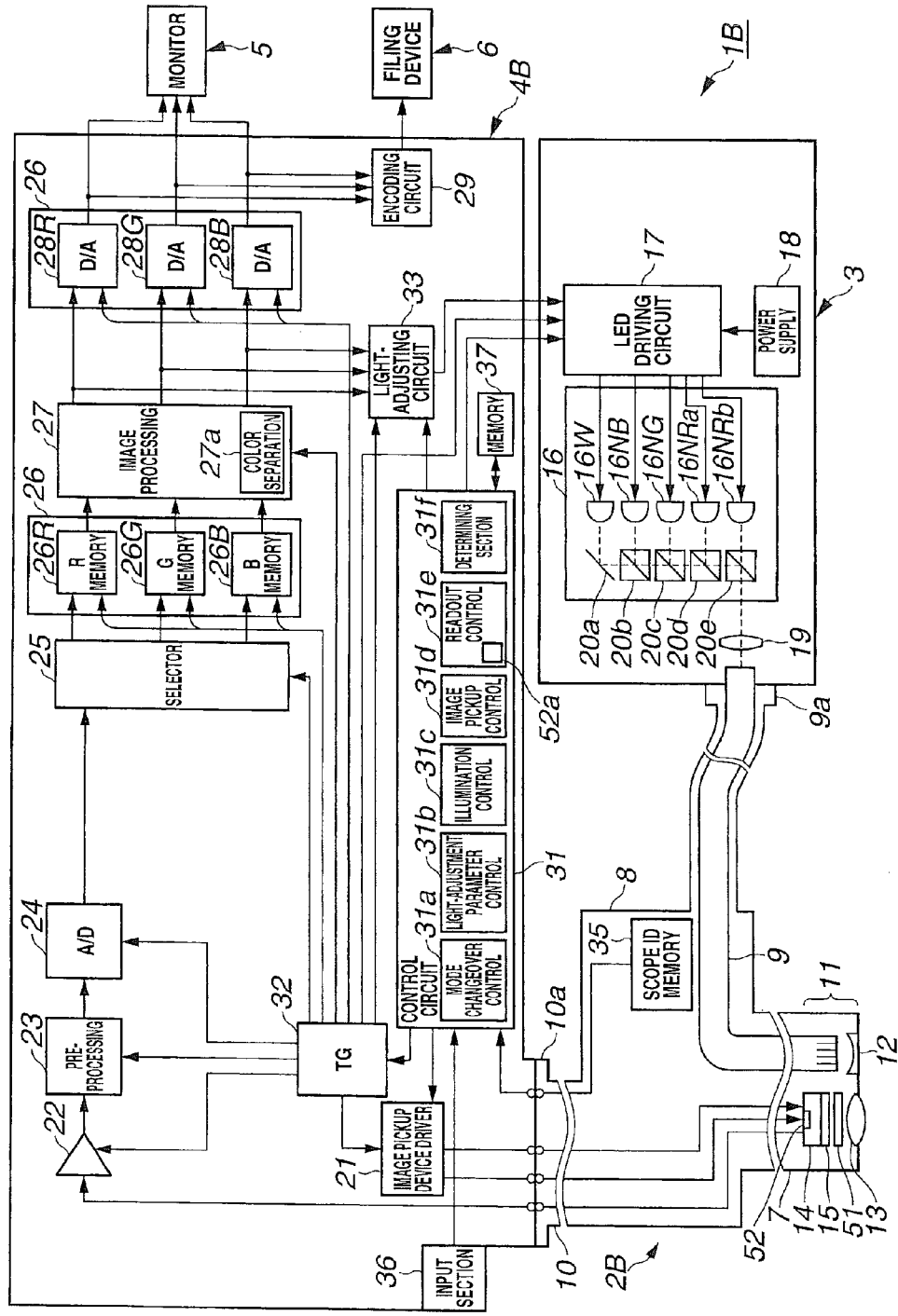
FIG. 10 is a diagram showing an overall configuration of an endoscope apparatus in a second embodiment of the present invention.

Next, a second embodiment of the present invention is explained with reference to FIG. 10. The present embodiment is an endoscope apparatus 1B enabled to perform a fluorescence observation. Besides the endoscope 2 shown in FIG. 1, an endoscope for fluorescence observation 2B shown in FIG. 10 is connected to the endoscope apparatus 1B to enable the endoscope apparatus 1B to perform the fluorescence observation.

In the endoscope for fluorescence observation 2B, an excitation light cut filter 51 that cuts excitation light is provided between the objective lens 13 and the image pickup device 14 in the endoscope 2 shown in FIG. 1. The image pickup device 14 includes a pixel binning circuit or a pixel binning section 52 configuring pixel addition and readout means for adding up and reading out an adjacent plurality of pixels besides normal readout for reading out, pixel by pixel, a picked-up signal of all pixels.

In a video processor 4B in the present embodiment, for example, the readout control section 31e in the control circuit 31 performs readout control for applying an image pickup device driving signal via the image pickup device driver 21, applying, to the image pickup device 14, a pixel binning control signal for adding up and reading out images of signals of all pixels picked up by the image pickup device 14, and adding up and reading out an output signal of an adjacent plurality of pixels such as two pixels or four pixels. That is, the readout control section 31e includes a pixel binning control section 52a. The endoscope for fluorescence observation 2B is an endoscope exclusive for fluorescence observation not including the mode changeover switch 34.

The video processor 4B in the present embodiment further includes a function of performing signal processing for a fluorescence observation mode in the video processor 4 shown in FIG. 1. The video processor 4B refers to information of the scope ID memory 35 and performs signal processing corresponding to the endoscope for fluorescence observation 2B. The light source device 3 has a configuration same as the configuration shown in FIG. 1. When the endoscope for fluorescence observation 2B is connected, the control circuit 31 controls the light source device 3 to perform generation of excitation light corresponding to the fluorescence observation mode and generation of reference light.

Figure 12:
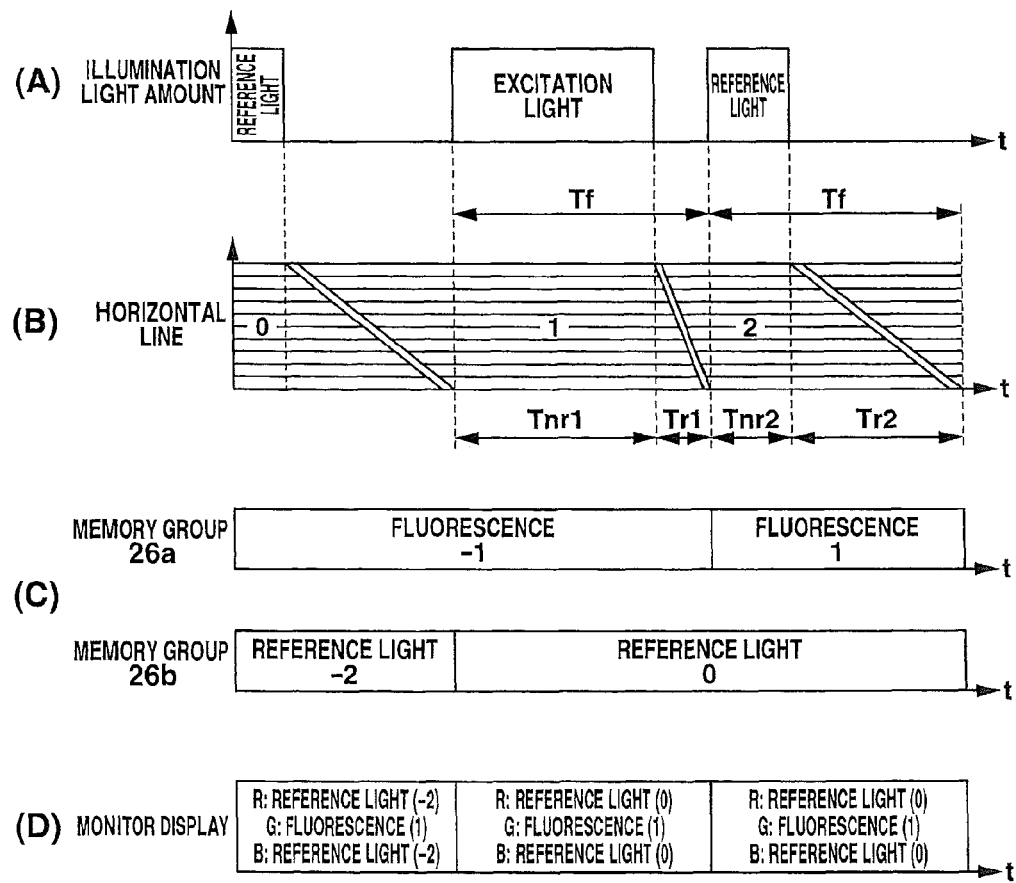
FIG. 12 is a timing chart for explanation in the case in which the fluorescence observation in the second embodiment is performed.

In this case, as explained below, in a case of the fluorescence observation mode in which the reference light and the excitation light are irradiated as illumination lights by illumination means and image pickup means performs a fluorescence observation for subjecting reflected light of the reference light and fluorescence to image pickup as return lights from an object, when the reference light and the excitation light are irradiated in a time division manner, the illumination control section 31c performs control to reduce, with pixel binning control means, a readout period for reading out a fluorescence signal of the fluorescence with respect to a readout period for reading out an image of a return light signal of the reflected light picked up by the image pickup means and increase, by the reduced period, an excitation light irradiation period for irradiating the excitation light. A specific example of this control is as shown in FIG. 12.

Figure 11:
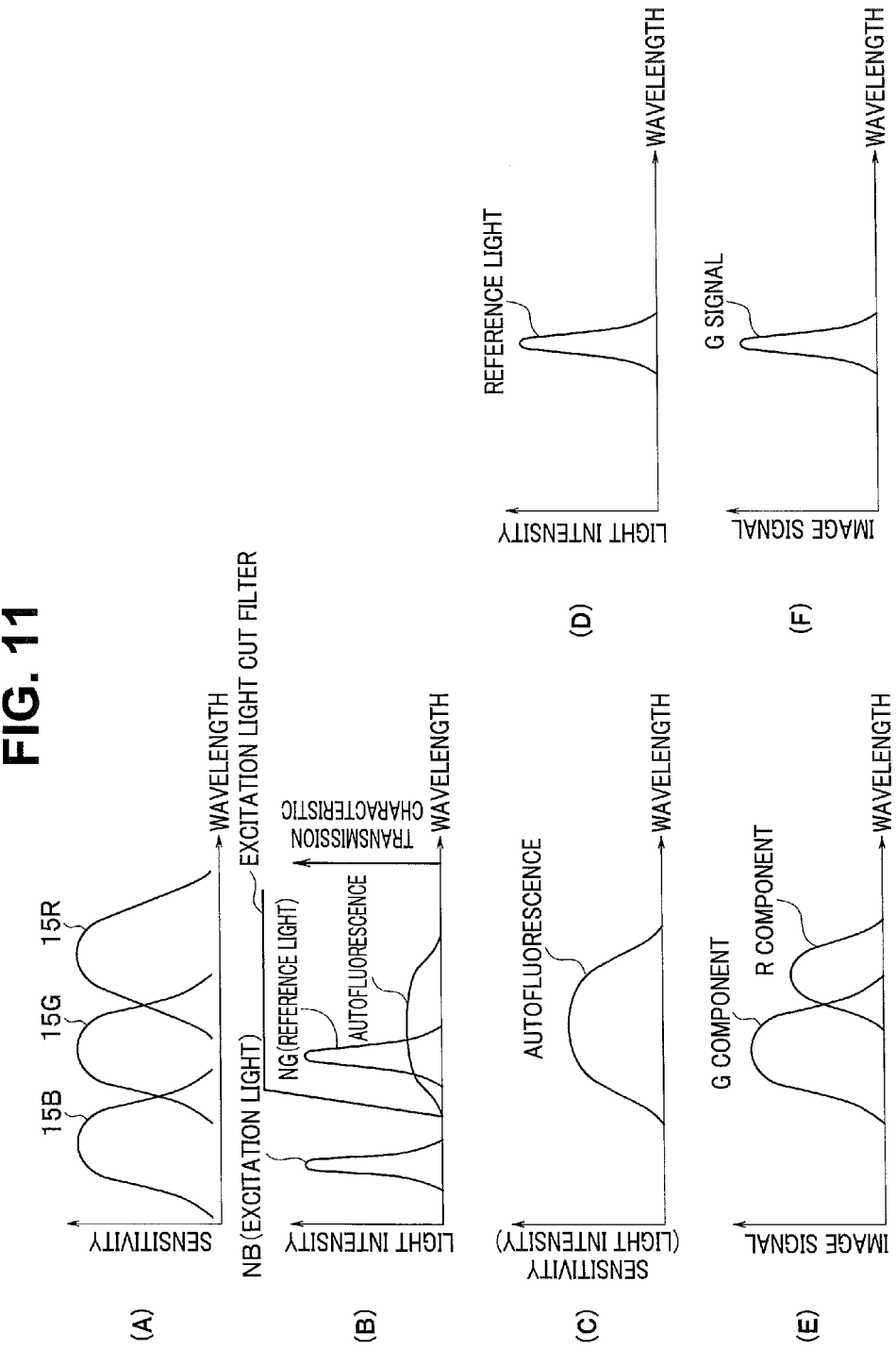
FIG. 11 is an explanatory diagram in a case in which a fluorescence observation in the second embodiment is performed.

FIG. 11 shows an explanatory diagram of an overall operation according to the present embodiment. FIG. 11(A) shows a filter characteristic of the color filter 15 same as the filter characteristic shown in FIG. 3(A). FIG. 11(B) shows light intensity of the excitation light and the reference light and a transmission characteristic of the excitation light cut filter 51.

In FIG. 11(B), a characteristic example of a wavelength band of an autofluorescence is also shown. In the present embodiment, the wavelength band of the autofluorescence is mainly a wavelength band of G. The wavelength band of the autofluorescence has a characteristic that a part of the wavelength band reaches a wavelength band of R. The wavelength band of G includes a wavelength band of the reference light. Therefore, it is difficult to sufficiently separate the autofluorescence and the reference light and subject the autofluorescence and the reference light to image pickup.

Therefore, in the present embodiment, irradiation of the excitation light and the reference light is performed in a time division manner. An irradiation time of the excitation light is increased to increase light intensity as shown in FIG. 11(C). In this case, sensitivity is also improved by pixel binning. Note that FIG. 11(D) shows light intensity of (return light of) the reference light irradiated at timing different from timing of the excitation light.

In this way, according to the time-division irradiation, an image signal of an image of the autofluorescence is acquired as shown in FIG. 11(E). An image signal of an image of the reference light is acquired as shown in FIG. 11(F).

As shown in FIG. 11(E), as the image signal of the image of the autofluorescence, an image signal obtained by adding up a G image component and an R image component is used. Note that a B image component is almost zero.

As shown in FIG. 11(F), as the image signal of the image of the reference light, only the G image component is used because the B image component and the R image component are almost zero.

Next, an operation in the present embodiment is explained with reference to a timing chart of FIG. 12.

The autofluorescence is an extremely dark image compared with a normal image or the NBI image. Therefore, it is desired to set an illumination time (an irradiation time) as long as possible. In the present embodiment, when the image of the autofluorescence is acquired, the illumination time of the excitation light is set large (long), signal intensity is increased using the pixel binning, and a number of pixels to be read out is reduced to reduce a readout time.

FIG. 12(A) shows timings of illumination or irradiation (exposure) of the illumination light (the excitation light). Readout of the CMOS sensor is performed as shown in FIG. 12(B) in synchronization with this illumination.

In the one frame period Tf, in a case of a fluorescence image, an illumination period is set longer than when a reference light image (a reflected light image) is acquired. The illumination period is a non-readout period Tnr1 for the fluorescence image. In a case of the reference light image, the illumination period is a shorter non-readout period (illumination period) Tnr2.

In the case of the reference light image, since a bright image is obtained, all pixels are read out in the readout period Tr2 without performing the pixel binning. On the other hand, in the case of the fluorescence image, readout is performed in the short readout period Tr1 using the pixel binning as explained above. For example, a number of pixels to be added when pixels are added by the pixel binning is set to four. The readout period Tr1 is reduced to ¼ of the readout period Tr2. The reduced period is allocated to the illumination period for the excitation light to increase the illumination period for the excitation light. In this way, one frame period in which the irradiation of the excitation light and the pixel readout (of the fluorescence) after the irradiation is performed is set to the one frame period Tf same as one frame period in which the irradiation of the reference light and the pixel readout (of the reference light image) after the irradiation is performed.

According to the illumination and the read out shown in FIG. 12(A) and FIG. 12(B), a fluorescence image and a reference light image are stored in the memory group 26a and the memory group 26b as shown in FIG. 12(C). The reference light image and the fluorescence image stored in the memory group 26a and the memory group 26b are outputted to the R, G, and B channels of the monitor 5 as shown in FIG. 12(D). The fluorescence image and the reference light image are superimposed and displayed in pseudo color on the display surface of the monitor 5.

According to the present embodiment, the endoscope 2 shown in FIG. 1 has the action and effects of the first embodiment. When the endoscope for fluorescence observation 2B shown in FIG. 10 is connected, the fluorescence observation can be performed.

Note that, in the present embodiment, the excitation light and the reference light are irradiated in a time division manner and the fluorescence image and the reference light image are acquired and displayed. However, near infrared fluorescence can also be observed using the image pickup device 14 including a color image sensor, that is, a color filter. A first modification of the present embodiment is explained.

Figure 13:
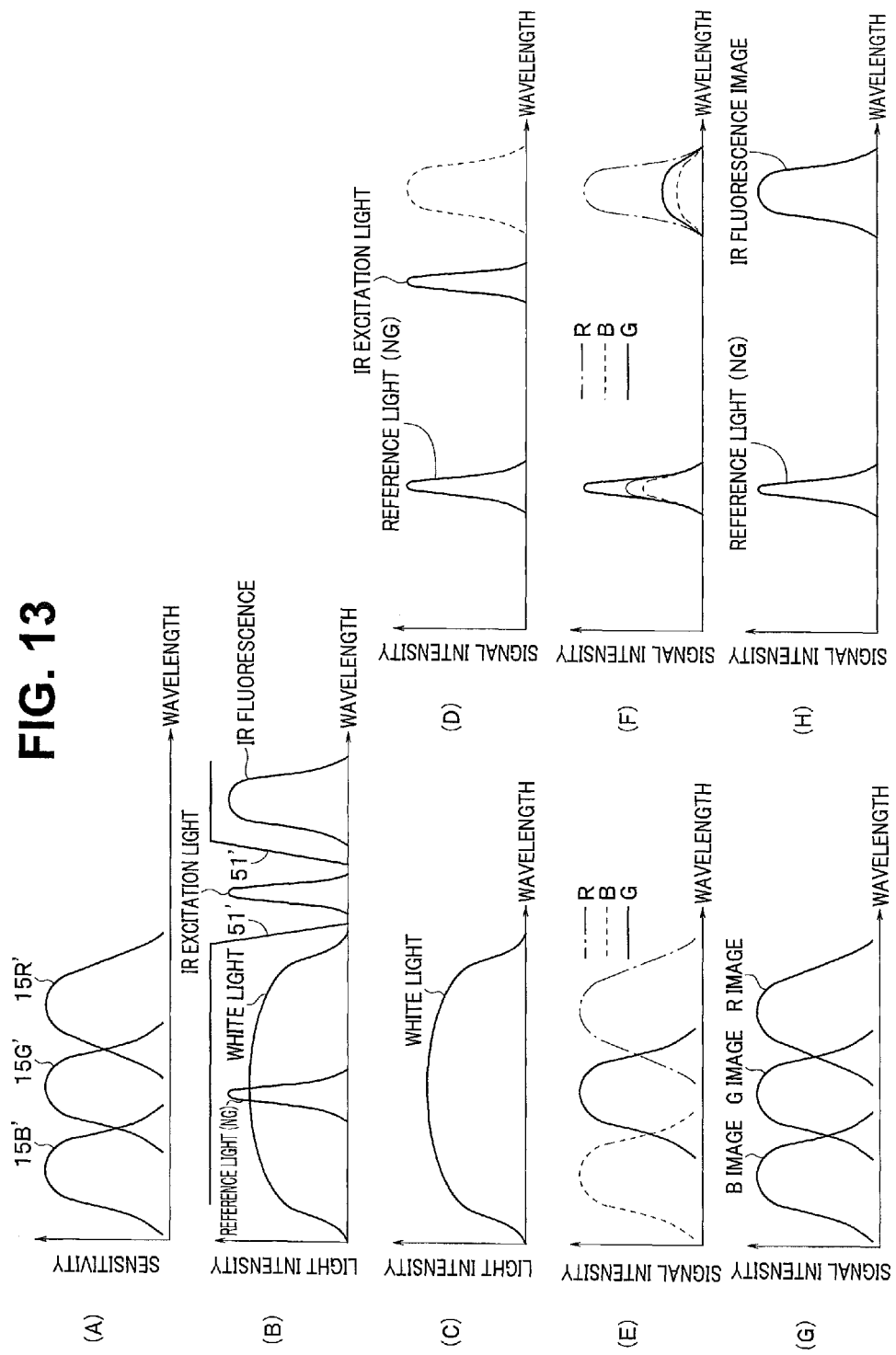
FIG. 13 is an operation explanatory diagram of a first modification of the second embodiment.

In this modification, in the endoscope for fluorescence observation 2B shown in FIG. 10, an excitation light cut filter 51' (see FIG. 13(B)) having a transmission characteristic for cutting excitation light different from the transmission characteristic of the excitation light cut filter 51 is adopted. An endoscope for fluorescence observation (hereinafter, 2B') including the R, G, and B filters 15R, 15G, and 15B of the color filter 15 having spectral characteristics slightly different from the spectral characteristics explained above is adopted.

In this modification, the light source device 3 shown in FIG. 10 further includes an LED that generates near infrared (IR) excitation light.

FIG. 13(A) shows spectral characteristics of R, G, and B filters 15W, 15G', and 15B' of the color filter 15 adopted in the endoscope for fluorescence observation 2B'. FIG. 13(B) shows light intensities of white light, reference light (15NG), IR excitation light, and IR fluorescence and a transmission characteristic (transmitted light intensity) of the excitation light cut filter 51'. Note that the reference light (15NG) is also referred to as G reference light.

In this modification, as shown in FIG. 13(B), the excitation light cut filter 51' is set to a characteristic for cutting a periphery of a wavelength band of the IR excitation light including the wavelength band and transmitting wavelength bands further on a short wavelength side (a wavelength band of visible light) and a long wavelength side (an IR fluorescence wavelength side) of the wavelength band of the IR excitation light.

As shown in FIG. 13(A), as the R, G, and B filters 15W, 15G, and 15B', filters having characteristics of transmitting wavelength bands further on a long wavelength side than wavelength bands of the R, G, and B filters 15W, 15G, and 15B', that is, having sensitivity even on the long wavelength side.

In this modification, as shown in FIG. 13(C) and FIG. 13(D), the WBI observation mode by white light and the fluorescence observation mode are performed in a time division manner. In other words, the simultaneous illumination system can be adopted as opposed to a case in which only the WBI observation mode or only the fluorescence observation mode is performed.

In a case of the WBI observation mode by the white light, the R, G, and B filters 15W, 15G, and 15B' are adopted, R, G, and B images are acquired by the characteristics of the signal intensities shown in FIG. 13(E), and the R, G, and B images are directly outputted to the monitor 5 as shown in FIG. 13(G).

On the other hand, in the fluorescence observation mode, as shown in FIG. 13(D), the IR excitation light and the reference light (NG light) are simultaneously irradiated. An image of the IR fluorescence further on the long wavelength side than the IR excitation light is picked up by the CMOS sensor. In FIG. 13(D), light intensity of the IR fluorescence is indicated by a dotted line. FIG. 13(F) shows a characteristic example of a signal intensity in a case in which image pickup is performed by the CMOS sensor in which the R, G, and B filters 15R, 15G', and 15B' shown in FIG. 13(A) are used.

FIG. 13(H) shows a signal intensity example in which a signal outputted in FIG. 13(F) is color-separated by the color separation circuit 27a.

Figure 14:
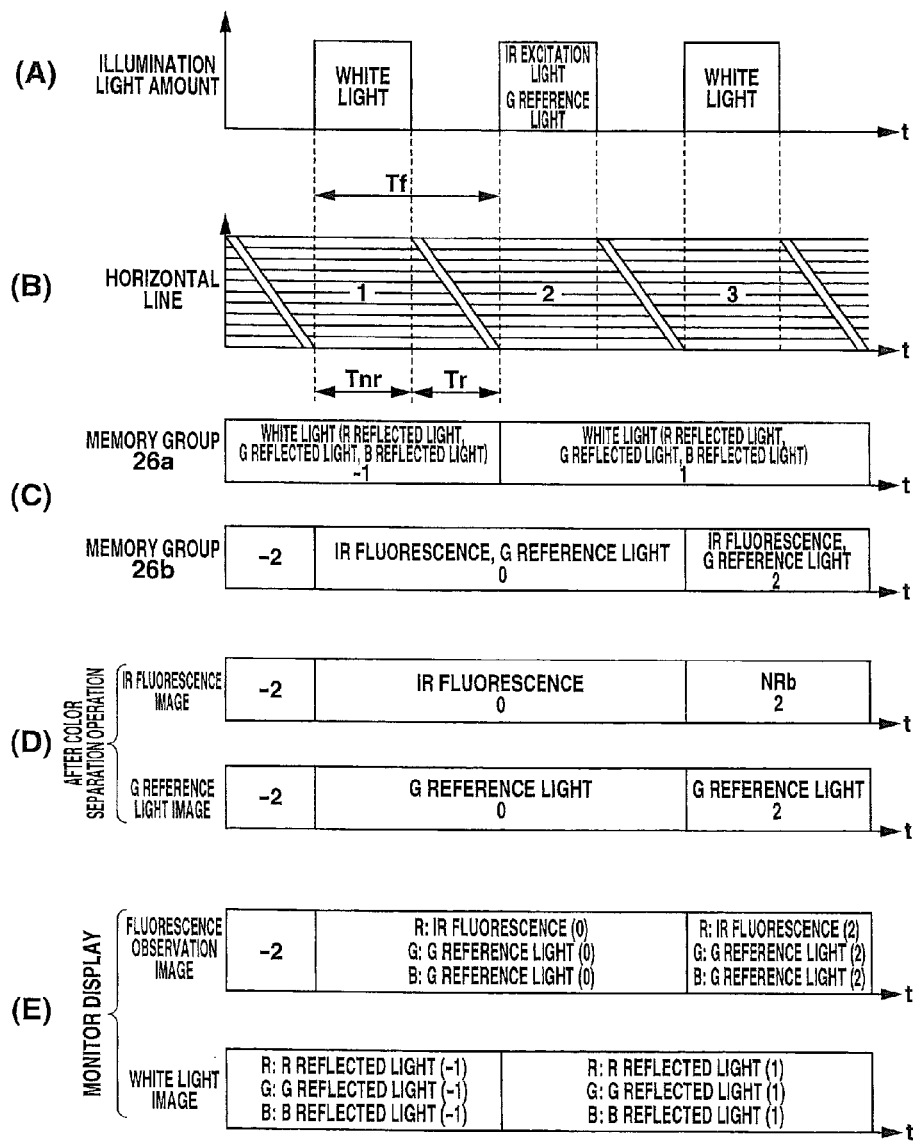
FIG. 14 is a timing chart for operation explanation of the first modification.

FIG. 14 shows operation contents using a timing chart according to this modification. As explained above, the WBI observation mode by white light and the fluorescence observation mode are performed in a time division manner. An image pickup system is the same as the image pickup system in a case of the time division in the first embodiment (the case of FIG. 9).

That is, when the NG light+the NRb light in FIG. 9 is replaced with white light and the NRa light in FIG. 9 is replaced with the IR excitation light and the G reference light, FIG. 14(A) and FIG. 14(B) are a same as FIG. 9(A) and FIG. 9(B). In this case, as shown in FIG. 14(C), image signals of white lights (R, G, and B reflected lights, in a broader sense, R, G, and B return lights) are stored as shown in FIG. 14(C). In the memory group 26b, image signals of the IR fluorescence and the G reference light are stored.

The image signals of the IR fluorescence and the G reference light in the memory group 26b are separated as shown in FIG. 14(D) by the color separation operation.

On the monitor 5, for example, as shown in FIG. 14(E), a fluorescence observation image is displayed in pseudo color in a state in which IR fluorescence, G reference light, and G reference light are allocated to the R, G, and B channels. On the other hand, a white light image is displayed in color in a state in which R, G, and B reflected light images are allocated (inputted) to the R, G, and B channels of the monitor 5.

According to this modification, when the fluorescence observation is performed, image signals simultaneously picked up by simultaneously irradiating the excitation light and the reference light can be color-separated and displayed as the fluorescence observation image.

Note that, in this modification, white light observation and IR fluorescence observation are performed in parallel. However, as a modification of this modification (a second modification of the second embodiment), when only the IR fluorescence observation is performed, the fluorescence observation image can be continuously obtained by simultaneously irradiating the IR excitation light and the G reference light. In this case, image pickup can be performed in a same manner as the case of the simultaneous illumination in the first embodiment (the case of FIG. 8).

Third Embodiment

Next, a third embodiment of the present invention is explained with reference to FIG. 15. In the first embodiment and the second embodiment, the endoscopes 2 and 2B including the progressive type image pickup device 14 capable of reading out all pixels of the image pickup surface 14a are explained. On the other hand, the present embodiment is an endoscope apparatus 1C enabled to perform WBI and NBI observations using, instead of the endoscope 2 including the progressive type image pickup device 14 in the endoscope apparatus 1 in FIG. 1, an endoscope 2C including an interlace type charge coupled device (abbreviated as CCD) 14C, which performs readout separately for even number lines and odd number lines, when all pixels (pixels for one frame) of the image pickup surface 14a are read out.

Figure 15:
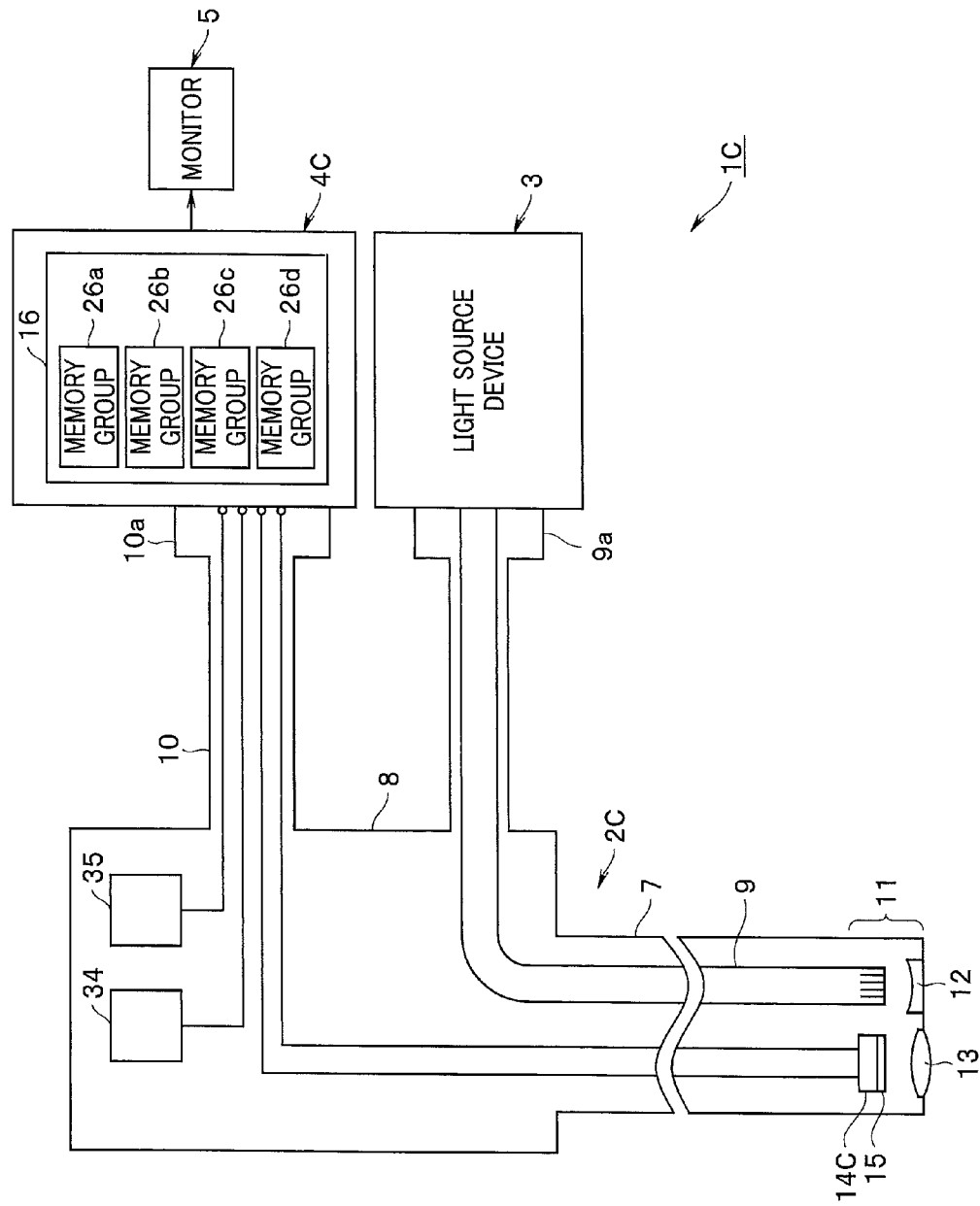
FIG. 15 is a diagram showing a schematic configuration of an endoscope apparatus in a third embodiment of the present invention.

In the endoscope apparatus 1C shown in FIG. 15, the image pickup device 14 in the endoscope 2 is changed to the interlace type CCD 14C functioning as an interlace type image pickup device and the memory section 26 in the video processor 4 is configured using the memory section 26 including the four memory groups 26a, 26b, 26c, and 26d in the endoscope apparatus 1 shown in FIG. 1. Otherwise, the endoscope apparatus 1C includes components same as the components in FIG. 1. FIG. 15 is simplified to clearly show only components different from the components shown in FIG. 1.

When the interlace type CCD 14C is used, since readout is alternately performed in even/odd fields, if the alternate irradiation of the two kinds of lights such as the NG light+the NRb light and the NRa light is repeated in the NBI observation mode as explained in the first embodiment, one light can obtain only one image signal of the even/odd fields.

Therefore, in the present embodiment, the control circuit 31 performs illumination control to change order of irradiation of the two kinds of illumination lights for each one frame period to eliminate omission in the respective fields and performs image pickup control (signal processing) corresponding to the illumination.

Therefore, in the present embodiment, (the readout control section 31e of) the control circuit 31 includes, in a case of a configuration in which image pickup means uses an interlace type image pickup device, readout control means for continuously reading out, when illumination lights in two or more different wavelength bands irradiated by illumination means are controlled to be time-divided into two and irradiated, pixels of odd lines and even lines in the interlace type image pickup device in a period in which the illumination light is irradiated twice in a time division manner in field period units.

Note that, in the present embodiment (and a modification explained below), the interlace type CCD 14C is explained as being capable of performing exposure and readout in each of one field pixel of an odd line and one field pixel of an even line.

Figure 16:
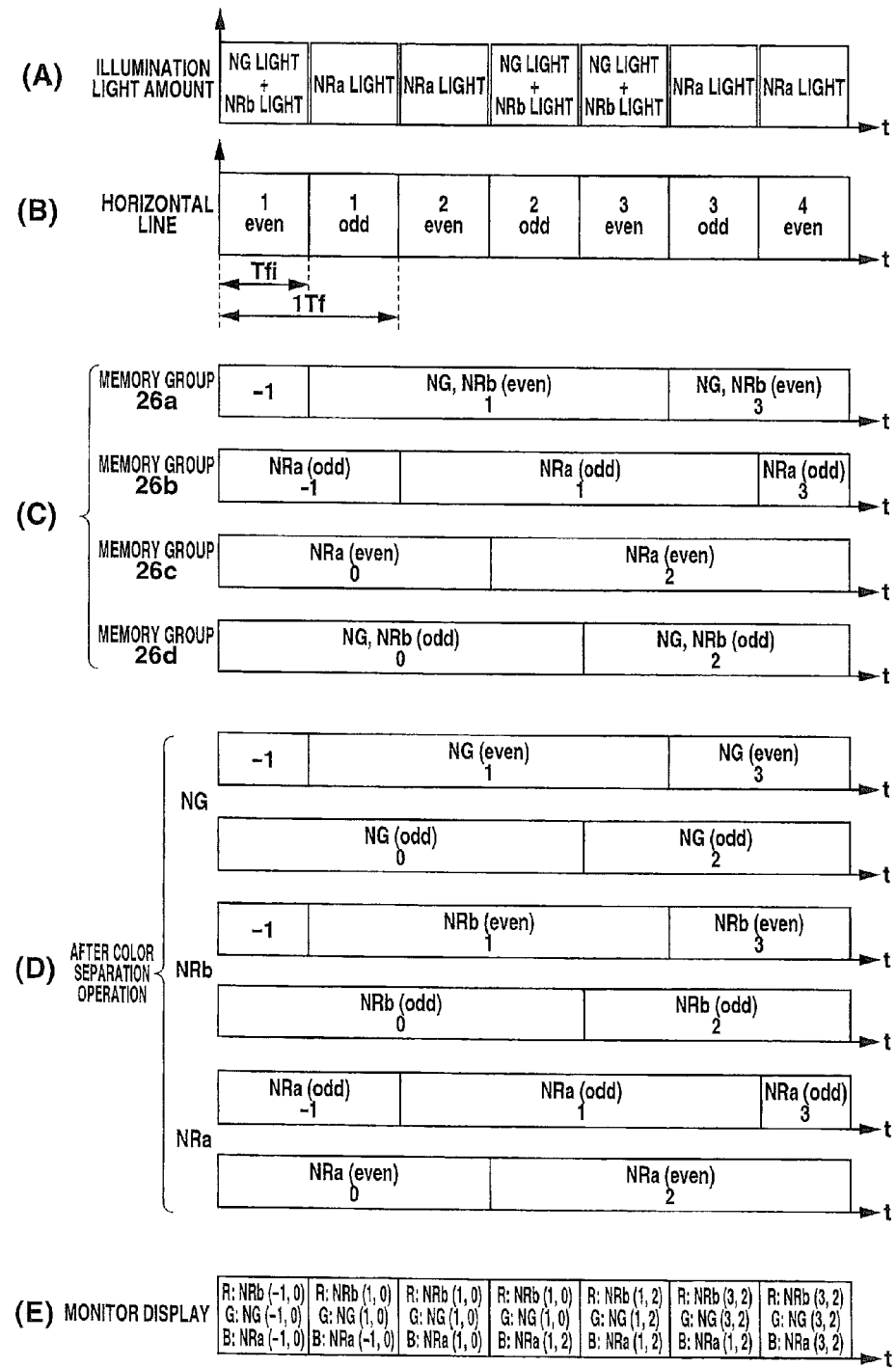
FIG. 16 is a timing chart for operation explanation in the third embodiment.

FIG. 16 shows a timing chart for operation explanation in the present embodiment. As explained above, when the irradiation of the NG light+the NRb light and the irradiation of the Na light are performed in the even/off fields, for example, in a first frame to prevent omission of a field from occurring in respective frames, as shown in FIGS. 16(A) and (B), in a second frame, irradiation of the Na light is performed in the even field and irradiation of the NG light+the NRb light is performed in the odd field. Note that a field period of the even field and the odd field is indicated by Tfi.

Image signals picked up by the interlace type CCD 14C according to such irradiation are stored in the four memory groups 26a to 26d as shown in FIG. 16(C). For example, image signals of NG and NRb picked up under the irradiation in the even field and the odd field of the NG light+the NRb light are stored in the memory groups 26a and 26d. Image signals of NRa respectively picked up under the irradiation in the even field and the odd field of the NRa light are stored in the memory groups 26b and 26c.

The image signals of NG and NRb picked up under the irradiation of the NG light+the NRb light are color-separated as shown in FIG. 16(D) by the color separation operation of the color separation circuit 27a.

The image signals of NRa picked up under the irradiation of the NRa light is outputted to a post stage side while keeping a state of FIG. 16(C) as shown in FIG. 16(D).

For example, as shown in FIG. 16(E), the NBI image is displayed in field period units on the monitor 5.

According to the present embodiment, even when the interlace type CCD 14C is used, it is possible to display the NBI image having resolution for one frame by performing time division illumination in which order of irradiating illumination light is changed in field units.

In the present embodiment, as in the first embodiment, it is possible to appropriately perform illumination control corresponding to the transmission wavelength characteristic of the color filter 15 of the image pickup device. The surgeon can smoothly perform an endoscopy with simple operation.

As explained above, in the present embodiment, the control is performed to change the order of irradiating the illumination light in a time division manner in the two field periods Tfi in the one frame period Tf. However, as a modification of the present embodiment, a line to be read out may be changed.

In this modification, (the readout control section 31e of) the control circuit 31 includes, in a case of a configuration in which image pickup means uses an interlace type image pickup device, readout control means for continuously and repeatedly reading out twice, when illumination lights in two or more different wavelength bands irradiated by illumination means are controlled to be time-divided into two and irradiated, pixels of odd lines or even lines in the interlace type image pickup device in a period in which the illumination light is irradiated twice in a time division manner in field period units.

In this modification, as shown in FIG. 17(A), with the one frame period Tf set as a cycle, the NG light+the NRb light and the NRa light are alternately irradiated as illumination light in units of the one field period Tfi.

In this case, when image pickup is performed by the CCD 14C as shown in FIG. 17(B), two times of readout in a same even field and a same odd field are repeatedly performed for each one frame period Tf.

In the case of irradiating two kinds of illumination lights as shown in FIG. 17, as shown in FIG. 17(A), in a first frame, after the NG light+the NRb light is irradiated in an even field period, the NRa light is irradiated in the even field period. In a following second frame, after the NG light+the NRb light is irradiated in an odd field period, the NRa light is irradiated in the odd field period.

In the respective fields, signals read out from the CCD 14C are stored in the memory groups 26a to 26d as shown in FIG. 17(C). Image signals of NG and NRb picked up under the irradiation of the NG light+the NRb light in the image signals stored in the memory groups 26a to 26d are color-separated as shown in FIG. 17(D) by the color separation operation of the color separation circuit 27a.

Image signals of NRa picked up under irradiation of the NRa light are outputted to the post stage side while keeping a state of FIG. 17(C) as shown in FIG. 17(D).

For example, as shown in FIG. 17(E), the NBI image is displayed in field period units on the monitor 5. In a case of FIG. 16, a case of timing when one field period is required to update an image of one wavelength band and a case of timing when three field periods are required are mixed. An update rate of an image is irregular. However, in a system in this modification, the image is always updated once in two field periods (i.e., one frame period). Therefore, when a moving image is displayed, there is an advantage that it is possible to eliminate irregularity (or discontinuity) of moving image display. Besides, the present modification has effects same as the effects of the third embodiment.

Note that embodiments configured by, for example, partially combining the embodiments including the modifications also belong to the present invention.

What is claimed is:

1. An endoscope apparatus comprising:
an illuminating section capable of irradiating, as illumination light for illuminating a subject, at least light in a first wavelength band and light in a second wavelength band having a wavelength band different from the light in the first wavelength band;
an image processing section for separating an image pickup signal generated in a first pixel that is provided in an endoscope for observing the subject and receives light in a predetermined wavelength band among lights from the subject on which the illumination light is irradiated and an image pickup signal generated in a second pixel that is provided in the endoscope and receives light in a wavelength band different from the light in the predetermined wavelength band among the lights from the subject into an image pickup signal corresponding to the first wavelength band and an image pickup signal corresponding to the second wavelength band;
a switch that switches observation modes by switching the light emitted by the illuminating section;
a control section that determines whether the image pickup signal generated in the first pixel and the image pickup signal generated in the second pixel can be separated into the image pickup signal corresponding to the first wavelength band and the image pickup signal corresponding to the second wavelength band based on information of the predetermined wavelength band corresponding to the first pixel provided in the endoscope, information of a wavelength band different from the predetermined wavelength band corresponding to the second pixel, information of the first wavelength band corresponding to the light in the first wavelength band irradiated by the illuminating section, information of the second wavelength band corresponding to the light in the second wavelength band irradiated by the illuminating section, when switching into an observation mode in which the light in the first wavelength band and the light in the second wavelength band are irradiated as the light irradiated by the illuminating section, by the switch; and
an illumination control section that controls the illuminating section to
simultaneously irradiates, when the control section determines that the image pickup signal generated in the first pixel and the image pickup signal generated in the second pixel can be separated into the image pickup signal corresponding to the light in the first wavelength band and the image pickup signal corresponding to the light in the second wavelength band, the light in the first wavelength band and the light in the second wavelength band and irradiates, in a time division manner, when the control section determines that the image pickup signals cannot be separated into the first image signal and the second image signal, the light in the first wavelength band and the light in the second wavelength band.

2. The endoscope apparatus according to claim 1, further comprising a readout control section that continuously reads out, within one frame period, when the illumination control section controls the light in the first wavelength band and the light in the second wavelength band irradiated by the illuminating section to be simultaneously irradiated, an image of a return light signal picked up in the first pixel and the second pixel and reads out, in the one frame period, for a predetermined period, when the illumination control section controls the light in the first wavelength band and the light in the second wavelength band irradiated by the illuminating section to be irradiated in a time division manner, the image of the return light signal picked up in the first pixel and the second pixel.

3. The endoscope apparatus according to claim 2, wherein, when the illumination control section controls the light in the first wavelength band and the light in the second wavelength band irradiated by the illuminating section to be irradiated in a time division manner, the illuminating section irradiates the illumination light in a period other than the predetermined period in the one frame period.

4. The endoscope apparatus according to claim 1, wherein the first pixel and the second pixel are pixels configuring an interlace type image pickup device, and the endoscope apparatus further comprises a readout control section that continuously and repeatedly reads out twice, when the illumination control section controls the light in the first wavelength band and the light in the second wavelength band irradiated by the illuminating section to be irradiated in a time division manner, pixels of an odd line or an even line in the interlace type image pickup device in a period in which the illumination light is irradiated twice in field period units in a time division manner.

5. The endoscope apparatus according to claim 1, wherein the image processing section applies, to an image pickup signal generated in the first pixel that receives the light in the predetermined wavelength band among the lights from the subject on which the illumination light is irradiated and an image pickup signal generated in the second pixel that receives the light in the wavelength band different from the light in the predetermined wavelength band among the lights from the subject, a color separation operation for respectively separating the image pickup signals into independent image components corresponding to the first wavelength band and the second wavelength band.

6. The endoscope apparatus according to claim 3, further comprising a pixel addition and readout section that adds up and reads out, when an image pickup section reads out the return light signal, signals of a plurality of pixels of an image pickup device configuring the image pickup section, wherein
in a case of a fluorescence observation mode in which the illuminating section irradiates reference light and excitation light as the illumination light and the image pickup section performs a fluorescence observation for picking up reflected light of the reference light and a fluorescence as return lights from the subject, when the reference light and the excitation light are irradiated in a time division manner,
the illumination control section performs control to reduce, with the pixel addition and readout section, a readout period for reading out a fluorescence signal of the fluorescence with respect to a readout period for reading out an image of a return signal of the reflected light picked up by the image pickup section and increase, by the reduced period, an excitation light irradiation period for irradiating the excitation light.

7. The endoscope apparatus according to claim 1, wherein the first pixel and the second pixel are provided in a CMOS sensor that performs read out in a rolling shutter system,
driving of the CMOS sensor is controlled not to include a non-readout period in which readout of the image signal is not performed when the control section determines that the image pickup signals can be separated, and is controlled to include the non-readout period when the control section determines that the image pickup signals cannot be separated, and
the illumination control section controls the illuminating section to simultaneously irradiate the light in the first wavelength band and the light in the second wavelength band when the control section determines that the image pickup signals can be separated, and controls the illuminating section to irradiate the light in the first wavelength band and the light in the second wavelength band to be switched intermittently for each non-readout period when the control section determines that the image pickup signals cannot be separated.

* * * * *